(12) United States Patent
Karpilow et al.

(10) Patent No.: US 10,137,188 B2
(45) Date of Patent: Nov. 27, 2018

(54) CELL LINES FOR VIRUS PRODUCTION AND METHODS OF USE

(71) Applicants: University of Georgia Research Foundation, Inc., Athens, GA (US); The United States of America, as represented by the Secretary, Department of Health and Human Services, Bethesda, MD (US); THERMO FISHER SCIENTIFIC INC., Waltham, MA (US)

(72) Inventors: Jon Michael Karpilow, Boulder, CO (US); Mark Steven Oberste, Johns Creek, GA (US); Ralph A. Tripp, Watkinsville, GA (US); Stephen M. Tompkins, Watkinsville, GA (US)

(73) Assignees: University of Georgia Research Foundation, Inc., Athens, GA (US); The United States of America, as represented by the Secretary, Dept. of Health and Human Services, Washington, DC (US); Thermo Fisher Scientific, Inc., Waltham, MA (US)

( * ) Notice: Subject to any disclaimer, the term of this patent is extended or adjusted under 35 U.S.C. 154(b) by 57 days.

(21) Appl. No.: 14/765,365

(22) PCT Filed: Feb. 5, 2014

(86) PCT No.: PCT/US2014/014813
§ 371 (c)(1),
(2) Date: Aug. 3, 2015

(87) PCT Pub. No.: WO2014/123967
PCT Pub. Date: Aug. 14, 2014

(65) Prior Publication Data
US 2015/0374812 A1 Dec. 31, 2015
US 2017/0151322 A9 Jun. 1, 2017

Related U.S. Application Data

(60) Provisional application No. 61/760,895, filed on Feb. 5, 2013, provisional application No. 61/885,357, filed on Oct. 1, 2013.

(51) Int. Cl.
| | |
|---|---|
| A61K 39/395 | (2006.01) |
| C07K 16/28 | (2006.01) |
| C12N 5/10 | (2006.01) |
| A61K 45/06 | (2006.01) |
| A61P 35/00 | (2006.01) |
| A61K 39/13 | (2006.01) |
| C12N 15/11 | (2006.01) |
| C12N 7/00 | (2006.01) |
| C12N 15/113 | (2010.01) |

(52) U.S. Cl.
CPC .............. *A61K 39/13* (2013.01); *C12N 7/00* (2013.01); *C12N 15/111* (2013.01); *C12N 15/113* (2013.01); *C12N 2310/14* (2013.01); *C12N 2310/141* (2013.01); *C12N 2320/12* (2013.01); *C12N 2770/32021* (2013.01); *C12N 2770/32034* (2013.01); *C12N 2770/32052* (2013.01); *C12N 2770/32351* (2013.01); *C12N 2770/32651* (2013.01)

(58) Field of Classification Search
CPC .... A61K 39/13; C12N 15/111; C12N 15/113; C12N 2310/14; C12N 2310/141
See application file for complete search history.

(56) References Cited

U.S. PATENT DOCUMENTS

| 8,188,060 | B2 | 5/2012 | Khvorova et al. | |
|---|---|---|---|---|
| 2006/0212950 | A1* | 9/2006 | Tuschl | A61K 48/0058 800/14 |
| 2009/0092616 | A1* | 4/2009 | Snyder | C07K 14/4702 424/139.1 |
| 2009/0280567 | A1 | 11/2009 | Leake et al. | |

FOREIGN PATENT DOCUMENTS

| JP | 2012/532616 A | 12/2012 |
|---|---|---|
| RU | 2 192 884 C2 | 11/2002 |
| WO | WO 97/08292 A1 | 3/1997 |
| WO | WO 2009/126308 A2 | 10/2009 |
| WO | WO 2011/006823 A1 | 1/2011 |

OTHER PUBLICATIONS

Iida et al., Free Radical Biology & Medicine, 2012: 1413-1422.*
Iida et al., Free Radical Biology & Medicine, 52, 2012:1413-1422.*
Belov et al., PLoS Pathog, 2008, 4(11):1-15.*
Gustafsson et al., Protein Expression and Purification, 2012, 83:37-46.*
Wiznerowicz et al., Journal of Virology, 2003, 77(16):8957-8961.*
Golden et al., PLOSone, 2013, 8(1):pdf pp. 1-10.*
Belov et al., A critical role of a cellular membrane traffic protein in poliovirus RNA replication, PLOS Pathogens, 2008, 4(11):pdf pp. 1-15.*
International PCT Application No. PCT/US2014/014813, filed Feb. 5, 2014; International Search Report and Written Opinion dated Sep. 10, 2014; 18 pages.
International PCT Application No. PCT/US2014/014813, filed Feb. 5, 2014; International Preliminary Report on Patentability dated Aug. 20, 2015; 12 pages.

(Continued)

*Primary Examiner* — Barry A Chestnut
(74) *Attorney, Agent, or Firm* — Mueting, Raasch & Gebhardt, P.A.

(57) ABSTRACT

Provided herein are engineered cell lines. In some embodiments, cells of an engineered cell line have altered expression of a gene and/or altered expression of an miRNA, wherein the altered expression results in increased or decreased production of a virus. The virus is a picornavirus, such as a poliovirus or Enterovirus 71. Also provided herein are methods for using the engineered cells to produce virus, and methods for treating a subject having or at risk of having a viral infection.

26 Claims, 17 Drawing Sheets

(56) References Cited

OTHER PUBLICATIONS

Figure 1:
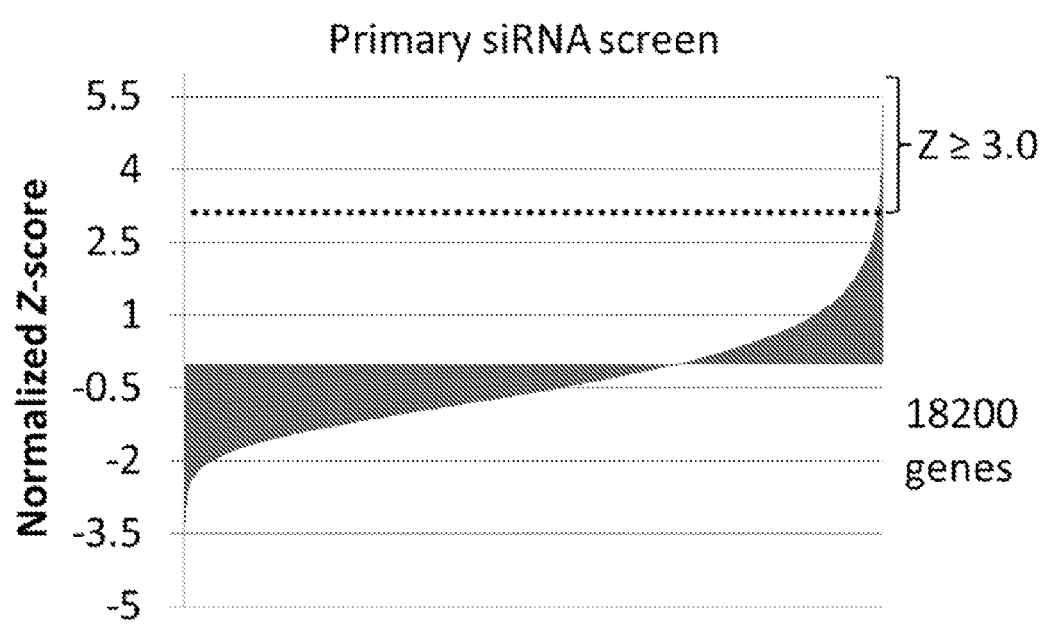

Belov et al. "A Critical Role of a Cellular Membrance Traffic Protein in Poliovirus RNA Replication" PLoS Pathogens, Nov. 2008; 4(11):e1000216. 16 pages.
Brass et al., "Identification of host proteins required for HIV infection through a functional genomic screen." Science, Feb. 15, 2008; 319(5865):921-6.
Carrington et al., "Role of microRNAs in plant and animal development" Science, Jul. 18, 2003; 301(5631):336-8.
Cherry, "Genome-wide RNAi screen reveals a specific sensitivity of IRES-containing RNA viruses to host translation inhibition" Genes Dev, 2005; 19:445-52.
Cronican et al. "Potent delivery of functional proteins into Mammalian cells in vitro and in vivo using a supercharged protein" ACS Chem Biol, 2010; 5(8):747-52.
Gibson et al. "Creation of a bacterial cell controlled by a chemically synthesized genome" Science, Jul. 2, 2010; 329(5987):52-6.
Griffiths-Jones, "The microRNA Registry" Nucleic Acids Res, Jan. 14, 200; 32(Database Issue):D109-11.
Hutvagner et al., "Sequence-specific inhibition of small RNA function" PLoS Biol., 2004; 2(4):E98.
Iida et al., "Identification of Rhit as a novel transcriptional repressor of human Mpv17-like protein with a mitigating effect on mitochondrial dysfunction, and its transcriptional regulation by FOXD3 and GABP" Free Radical Biology Med, 2012; 52:1413-22.
Karlas et al., "Genome-wide RNAi screen identifies human host factors crucial for influenza virus replication" Nature Letters, Feb. 2010; 463: 818-24.
Kolokoltsov et al., "Small interfering RNA profiling reveals key role of clathrin-mediated endocytosis and early endosome formation for infection by respiratory syncytial virus" J Virol, 2007; 81(14):7786-800.
Konig et al., "Global analysis of host-pathogen interactions that regulate early-stage HIV-1 replication" Cell, 2008; 135:49-60.
Meister et al., "Sequence-specific inhibition of microRNA- and siRNA-induced RNA silencing" RNA, Mar. 2004; 10(3):544-50.
Perwitasari et al., "siRNA Genome Screening Approaches to Therapeutic Drug Repositioning" Pharmaceuticals, 2013; 6:124-60.
Ramos et. al. "Cell receptors for influenza a viruses and the innate immune response" Front Microbiol, Mar. 28, 2012; 3:117.
Shangary et. al., "Small-molecule inhibitors of the MDM2-p53 protein-protein interaction to reactivate p53 function: a novel approach for cancer therapy" Annu Rev Pharmacol Toxicol, 2009; 49:223-41.
Van der Sanden et al., "Engineering Enhanced Vaccine Cell Lines to Eradicate Vaccine-Preventable Diseases: the Polio End Game" J Virol, Feb. 2016; 90(4):1694-1704.
Van der Sanden et al., "Engineering Enhanced Vaccine Cell Lines to Eradicate Vaccine-Preventable Diseases: the Polio End Game—Supplemental Tables" J Virol, Feb. 2016; 90(4): 395 pages.
Vermeulen et al., "Double-stranded regions are essential design components of potent inhibitors of RISC function" RNA, May 2007; 13(5):723-30.
Zhang et al. "A Simple Statistical Parameter for Use in Evaluation and Validation of High Throughput Screening Assays" J Biomol Screen, 1999; 4(2):67-73.
Wu et al., "The Use of RNAi Technology in the Development of High Performance Bioproduction Cell Lines" in *Frontiers in RNAi*. Tripp and Karpilow (Eds.) Bentham Science Publishers Ltd.: Sharjah, U.A.E.; 2014. Cover page, publisher's page, Table of Contents and pp. 232-246.
Proud et al., "Gene Expression Profiles during In Vivo Human Rhinovirus Infection: Insights into the Host Response" Am J Respir Crit Care Med, 2008; 178:962-8.
Friedel and Haas, "Microbial systems biology: Virus—host interactomes and global models of virus-infected cells" Trends in Microbiology, Oct. 19, 2011, (10):501-8. Epub Aug. 18, 2011.
European Patent Application No. 18164513.6, filed Mar. 28, 2018 (Priority Filing Date: Feb. 5, 2014); Partial Search Report dated Jun. 12, 2018; 12 pages.

* cited by examiner

A.

B.

Figure 4

Antigen equivalency testing

| CONTROL | 1:144 |
|---|---|
| BCL9 | 1:144 |
| BTN2A1 | 1:181 |
| CNTD2 | 1:288 |
| COLEC11 | 1:181 |
| DPM2 | 1:455 |
| EP300 | 1:144 |
| ETS1 | 1:181 |
| GLRXP3 | 1:181 |
| GPR30 | 1:144 |
| LY6G6C | 1:288 |
| MCCD1 | 1:181 |
| MED31 | 1:227 |
| PATE2 | 1:144 |
| PKIg | 1:144 |
| SEC61A1 | 1:144 |
| SIN3B | 1:144 |
| SLC1A2 | 1:144 |
| ZNF205 | 1:181 |

Effects of Gene Knockdown on Sabin 3, Plaque Assays

CCID-50 Validation of microRNA pro-virus hits in VERO P cells

Plaque assay on RD cells; 10^5 dilutions shown

NTC　　　ZNF205　　　CNTD2　　　MCCD1

CELL LINES FOR VIRUS PRODUCTION AND METHODS OF USE

CROSS-REFERENCE TO RELATED APPLICATIONS

This application is the § 371 U.S. National Stage of International Application No. PCT/US14/14813, filed Feb. 5, 2014, which claims the benefit of U.S. Provisional Application Ser. No. 61/760,895, filed Feb. 5, 2013, and 61/885,357, filed Oct. 1, 2013, each of which is incorporated by reference herein in their entireties.

GOVERNMENT FUNDING

The present invention was made with government support under Federal budget line 5614A11101 "Emerging Infections." The government has certain rights in this invention.

FIELD OF THE INVENTION

The invention relates to compositions and methods for enhancing the production of a virus. Specifically, the compositions may include genes (gene targets), effectors of said gene targets, as well as cell lines and cell lysates in which the gene targets have been altered to enhance virus production.

BACKGROUND

Vaccines are one of the chief strategies employed to prevent human disease. Currently over two dozen vaccines are available to combat diseases caused by viral (e.g., chickenpox, hepatitis B, measles, polio) and bacterial contagions (e.g., cholera, tetanus, typhoid, diphtheria). Similarly, vaccines are used to prevent a host of afflictions in domesticated animals including but not limited to poultry, horses, pigs, and other animals.

While several vaccines (including influenza vaccines) are still produced in fertilized chicken eggs (*Gallus gallus domesticus*), the greater number of vaccines are produced in cell culture. In one instance, well characterized cell lines (e.g., Vero Cells) are first infected with live or live-attenuated viruses. Subsequently, the supernatant containing progeny viral particles is collected and processed to create highly immunogenic doses of vaccine that can then be distributed amongst the population.

Despite the demonstrated success of vaccines, the ability to eradicate or manage disease outbreaks is repeatedly challenged by the costs and manufacturing limitations of vaccine production. This is best illustrated with polio vaccines. Poliovirus is a human enterovirus and the causative agent of poliomyelitis, an acute paralysis resulting from fecal-oral transmission of this neuro-degenerative agent. At this time, vaccines have been created to limit the spread of polio, and include the high effective (and significantly more expensive) inactivated polio vaccine (IPV), the less efficacious (and more economical) oral polio vaccine (OPV). For technical reasons related to the reversion of attenuated OPV virus particles to highly infectious neurovirulent poliovirus, successful eradication of polio will be aided by the development of new technologies that significantly decrease IPV manufacturing costs.

SUMMARY OF THE INVENTION

Provided herein is a collection of genes, reagents, and cell lines that can be used by polio vaccine manufacturers to significantly reduce production costs of OPV and IPV vaccines. The present invention provides a list of host genes (protein encoding genes and non-coding RNAs) that when modulated (either down-regulated or over-expressed) enhance poliovirus replication. As such, the identified genes can be modulated to increase poliovirus vaccine production. Furthermore, the inventors describe a series of cell lines that can be generated to enhance the production of poliovirus. All of the above can be used, separately or in combination, to enhance the production of vaccines used to combat polio and other picornavirus infections. Lastly, the inventors describe a series of genes that can be modulated by a number of means (e.g., siRNAs, miRNAs, small molecules) to limit poliovirus production.

Provided herein are engineered cell lines. In one embodiment, cells of the engineered cell line have decreased expression of a coding region selected from Table I compared to a control cell line, wherein the coding region is selected from ZNF205, CNTD2, SEC61G, ETS1, TAF1L, MCCD1, LY6G6C, BTN2A1, GLXP3, GCGR, EP300. In one embodiment, cells of the engineered cell line have decreased expression of a coding region selected from Table I compared to a control cell line. The decrease may be at least 5% compared to the control cell line. The decrease in expression may be determined by measuring the amount in the cells of polypeptide or mRNA encoded by the coding region. In one embodiment, the cells include a mutation in the coding region or in a regulatory region operably linked to the coding region. In one embodiment, the cells include an exogenous polynucleotide that decreases the expression of the coding region. The exogenous polynucleotide may be an RNA polynucleotide, such as a siRNA, a shRNA, or an antisense polynucleotide. In one embodiment, the cells include an edited genome that results in the decreased expression. For instance, the genome may be edited by a zinc finger nuclease, a meganuclease, or a transcription activator-like effector.

In one embodiment, the cells further include decreased expression of at least one additional coding region selected from Table I, increased expression of an miRNA selected from miR-520e, miR-1256, miR-520d-3p, miR-513a-5p, miR-519c-3p, miR-1270-2, miR-3187, miR-5763p, miR-22, miR-520c-3p, and miR-9 compared to a control cell line, decreased expression of an miRNA selected from Table IV, or a combination thereof. In one embodiment, the cells include decreased expression of at least five coding regions selected from Table I. In one embodiment, the cells further include decreased expression of a combination of at least 2 coding regions, wherein the combinations of coding regions are selected from Table VI. In one embodiment, the cells include increased expression of a coding region selected from Table II compared to a control cell line. In one embodiment, the cells further include increased expression of at least one additional coding region selected from Table II, decreased expression of an miRNA selected from miR-520e, miR-1256, miR-520d-3p, miR-513a-5p, miR-519c-3p, miR-1270-2, miR-3187, miR-5763p, miR-22, miR-520c-3p, and miR-9 compared to a control cell line, decreased expression of an miRNA selected from Table IV, or a combination thereof. In one embodiment, the cells include increased expression of at least five coding regions selected from Table II.

In one embodiment, cells of the engineered cell line include increased expression of an miRNA selected from miR-520e, miR-1256, miR-520d-3p, miR-513a-5p, miR-519c-3p, miR-1270-2, miR-3187, miR-5763p, miR-22, miR-520c-3p, and miR-9 compared to a control cell line.

The cells may include an miRNA mimic that behaves like one of the miRNAs. In one embodiment, the cells further include increased expression of at least two miRNAs.

In one embodiment, cells of the engineered cell line include decreased expression of an endogenous miRNA selected from Table IV compared to a control cell line. In one embodiment, the cells include a mutation in the coding region encoding the miRNA or in a regulatory region operably linked to the coding region. In one embodiment, the cells include an miRNA inhibitor that inhibits activity of the endogenous miRNA.

The cells of an engineered cell line may include a picornavirus. In one embodiment, the picornavirus is a poliovirus, such as an attenuated polivirus, e.g., Sabin 1, Sabin 2, Sabin 3. In one embodiment, the poliovirus is selected from Mahoney, Brunhilde, MEF-1, Saukett, or a combination thereof. In one embodiment, cells of the cell line include two or three polioviruses. In one embodiment, the picornavirus is enterovirus 71.

The engineered cell line may be a mammalian cell line, an avian cell line, or an insect cell line. In one embodiment, the mammalian cell line is selected from a human cell line, a non-human primate cell line, a canine cell line, or a hamster cell line. In one embodiment, the mammalian cell line is HEp-2 or Vero P. In one embodiment, the avian cell line is a chicken cell line, or a duck cell line.

Further provided herein is a lysate of an engineered cell line.

Provided herein are methods for producing a virus. In one embodiment, the method includes providing the engineered cell line described herein wherein cells of the cell line include a virus, incubating the engineered cell line under conditions suitable for the production of the virus by the cells, optionally, harvesting the virus produced by the cells. In one embodiment, the method includes providing a cell line wherein cells of the cell line include a virus, incubating the cell line under conditions suitable for the production of the virus by the cells, wherein the medium includes an RNA polynucleotide that inhibits expression of a coding region selected from Table I, and optionally harvesting the virus produced by the cells. In one embodiment, the RNA polynucleotide may be a siRNA, a shRNA, or an antisense polynucleotide, an miRNA selected from miR-520e, miR-1256, miR-520d-3p, miR-513a-5p, miR-519c-3p, miR-1270-2, miR-3187, miR-5763p, miR-22, miR-520c-3p, and miR-9, an mRNA inhibitor that inhibits activity of an miRNA selected from Table IV, or a combination thereof.

In one embodiment, the method includes providing a cell line wherein cells of the cell line include a virus, and wherein the cells include an edited genome that results in decreased expression of a coding region selected from Table I, incubating the cell line under conditions suitable for the production of the virus by the cells, and optionally harvesting the virus produced by the cells. In one embodiment, the genome is edited by a zinc finger nuclease, a meganuclease, or a transcription activator-like effector. In one embodiment, the method includes providing a cell line wherein cells of the cell line include a virus, incubating the cell line under conditions suitable for the production of the virus by the cells, wherein the medium includes a small molecule that inhibits expression of a coding region selected from Table I, and optionally harvesting the virus produced by the cells.

The cells used in a method may include a picornavirus. In one embodiment, the picornavirus is a poliovirus, such as an attenuated polivirus, e.g., Sabin 1, Sabin 2, Sabin 3. In one embodiment, the poliovirus is selected from Mahoney, Brunhilde, MEF-1, Saukett, or a combination thereof. In one embodiment, the cells used include two or three polioviruses. In one embodiment, the picornavirus is enterovirus 71.

The cells used in a method may be a mammalian cell line, an avian cell line, or an insect cell line. In one embodiment, the mammalian cell line is selected from a human cell line, a non-human primate cell line, a canine cell line, or a hamster cell line. In one embodiment, the mammalian cell line is HEp-2 or Vero P. In one embodiment, the avian cell line is a chicken cell line, or a duck cell line.

Also provided are methods for treating a subject having or at risk of having a viral infection. In one embodiment, the method includes increasing, in cells of the subject, expression of a coding region selected from Table I. In one embodiment, the method includes inhibiting, in cells of the subject, expression of a coding region selected from Table II. In one embodiment, the method includes inhibiting expression, in cells of the subject, of an endogenous miRNA selected from miR-520e, miR-1256, miR-520d-3p, miR-513a-5p, miR-519c-3p, miR-1270-2, miR-3187, miR-5763p, miR-22, miR-520c-3p, and miR-9. In one embodiment, the method includes increasing, in cells of the subject, expression of an miRNA selected from Table IV.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

BRIEF DESCRIPTION OF THE FIGURES AND TABLES

FIG. 1. Results of Primary Genome-wide siRNA Screen. Graph shows the results of screening >18,200 genes using a poliovirus-specific ELISA. The virus used in these screens was Sabin 2. Y axis provides normalized Z-score. X-axis represents genes screened.

Figure 2:
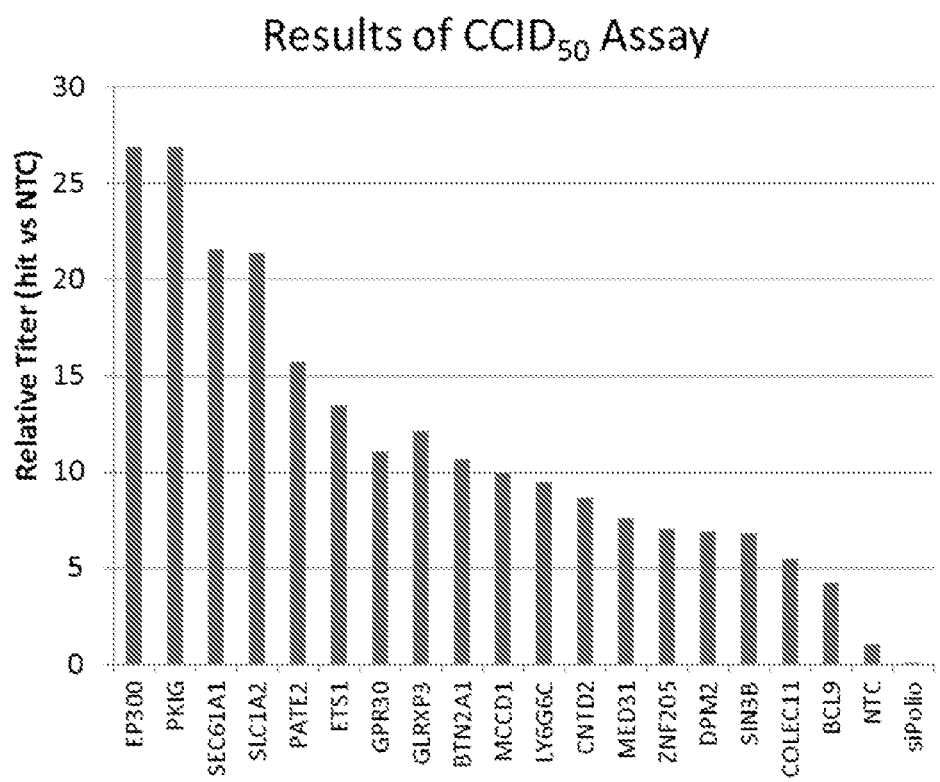

FIG. 2. Results of $CCID_{50}$ Assay. Graph shows how knockdown of a collection of exemplary individual genes in Vero Cells affects viral titer. Y-axis, viral titer normalized to Non-Targeting Control (NTC). The virus used in these screens was Sabin 2. X-axis provides gene names.

Figure 3:
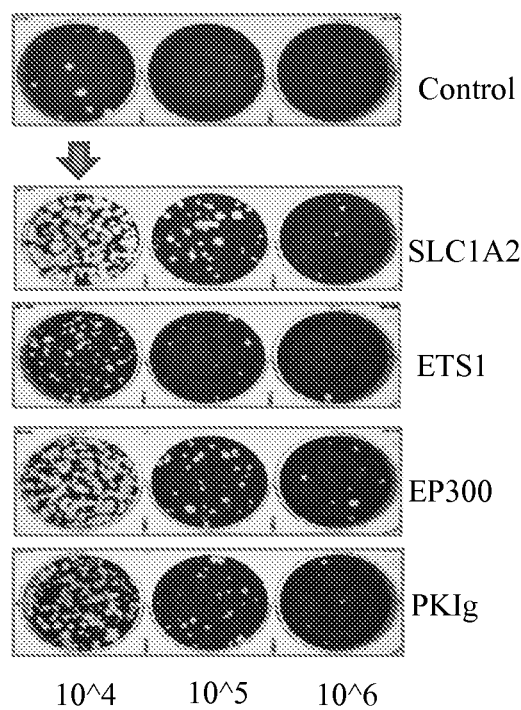
Figure 3:
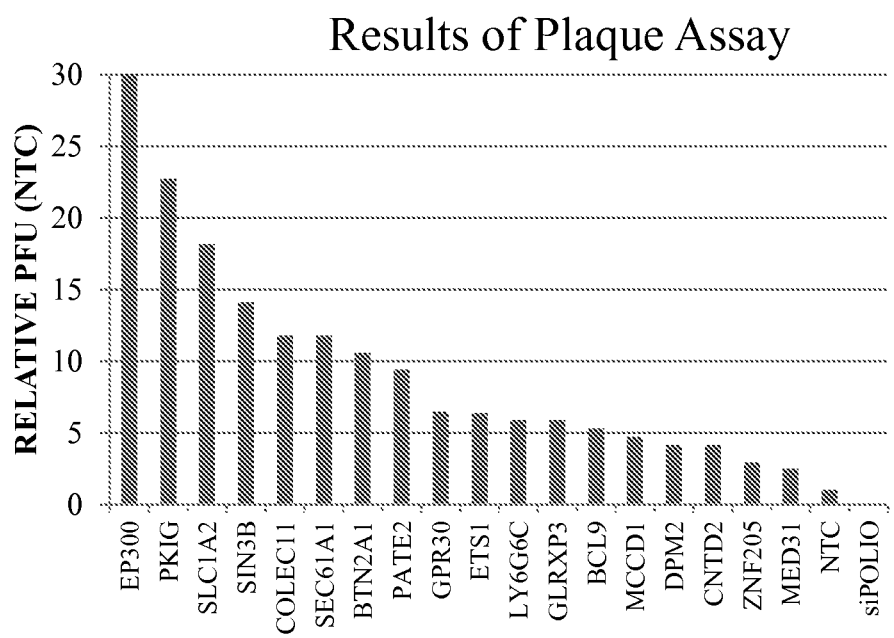

FIG. 3. Results of Plaque Assays. (A) Figure provides examples of how knockdown of target genes identified in the primary screen increases overall plaque number (virus titer, i.e., amount of virus). Control=Non-Targeting Control siRNA. Supernatant dilutions range from $10^{-4}$ to $10^{-6}$. (B) Graph shows the results from a collection of hits identified in the primary ELISA screen. NTC=Non-Targeting Control.

siPolio=siRNAs targeting the poliovirus genome. The virus used in these screens was Sabin 2.

FIG. 4. Results of Antigen Equivalency Studies. Antigen equivalency studies were performed on virus produced in Vero cells that were unmodified or modified with siRNA targeting specific genes. The numbers indicate the dilution of a standardized human serum pool that neutralizes the infectivity of virus derived from the given gene knockdown.

FIG. 5. Results of Poliovirus Types 1 and 3 (Sabin Strains). Vero cells transfected with siRNA targeting genes identified in the primary (Sabin 2) screen were subsequently infected with (A) poliovirus type 1 (Sabin strain), or (B) poliovirus type 3 (Sabin). Subsequent supernatants were assessed using the poliovirus ELISA described in Example 1. Vero cells transfected with siRNA targeting genes identified in the primary screen were subsequently infected with (C) poliovirus type 1 (Sabin strain), or (D) poliovirus type 3 (Sabin). Subsequent supernatants were assessed using the plaque assay described in Example 1.

Figure 6:
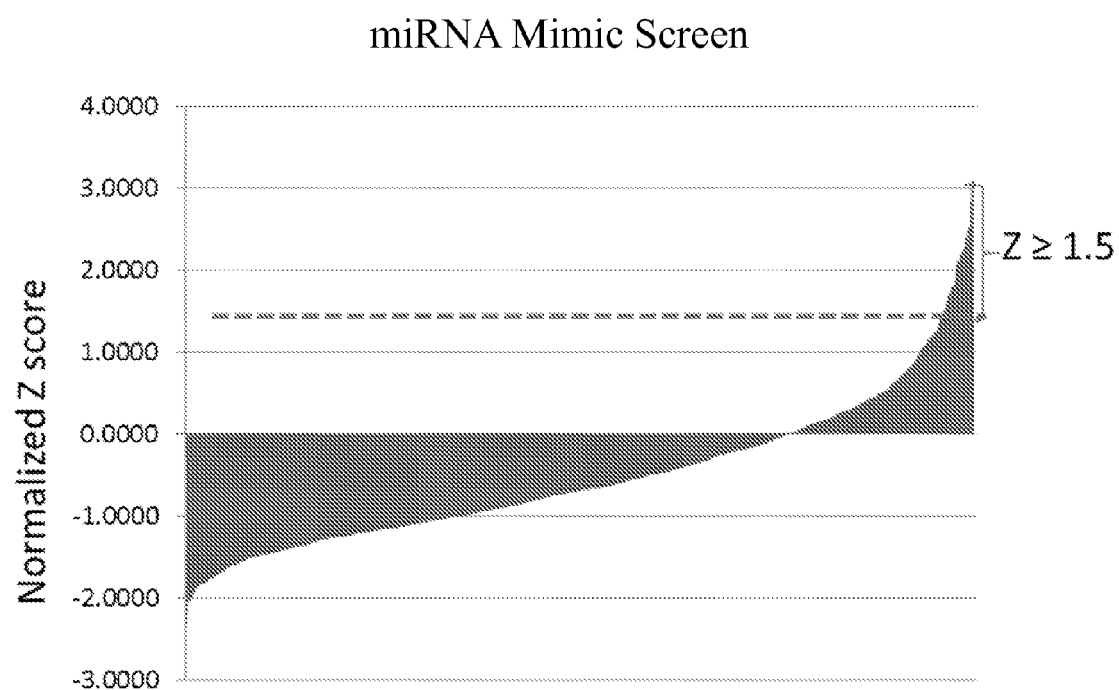

FIG. 6. Summary of miRNA mimics screen. Greater than 1,200 miRNA mimics were tested in the primary ELISA screen to identify genes that enhanced and decreased poliovirus antigen.

Figure 7:
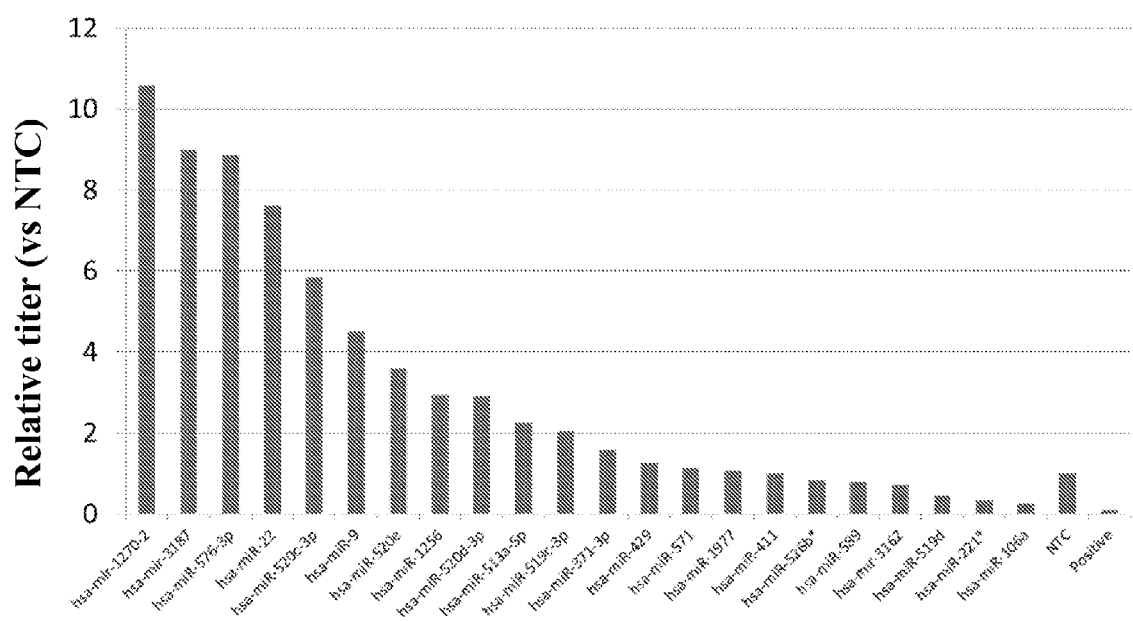

FIG. 7. Performance of individual miRNA mimics in $CCID_{50}$ assay. Eleven miRNAs identified in the primary screen induce two-fold or greater increases in viral titer.

FIG. 8. A. Exemplary gene knockdown (KD) data. q-RT-PCR was used to assess the level of target gene knockdown following transfection of individual siRNA into Vero cells. Results for nine gene silencing experiments (ZNF205, SEC61G, ETS1, EP300, BTN21A, GLRXP3, TAF1, MCCD1, and GCGR) show that 70% KD or greater is typically observed. B. Graph shows the effects of single gene knockdown events on seven different polioviruses. Twenty-nine separate genes were individually silenced in Vero cells. Subsequently, cells were infected with one of seven different polio strains including Sabin 1, Sabin2, Sabin 3, Mahoney (wild type 1), Brunhilde (wild type 1), MEF (wild type 2), and Saukett (wild type 3). Reported titers are relative to those observed when a non-targeting control siRNA (NTC) is transfected into cells. Additional controls include 1) a pool of siRNA targeting the poliovirus (siPolio), mock infections (Mock), and cells treated with lipid transfection reagents in the absence of siRNA (-siRNA). Solid line indicates a four-fold increase in viral titer. Dotted line indicates an increase of eight-fold (or better) in viral titers. This data provides further support that knockdown of the gene targets identified in the primary screen leads to enhancement of poliovirus production.

FIGS. 9 A and B. Exemplary data of the effects of dual gene knockdown on the titer of multiple poliovirus strains. Dark grey bars represent actual increase in viral titers observed when both genes were silenced simultaneously. Light grey bars represent predicted titers based on sum of observed changes when individual genes are silenced. "*" represents incidents where observed increases in titer are greater than sum of individual events ($P<0.05$).

Figure 10A:
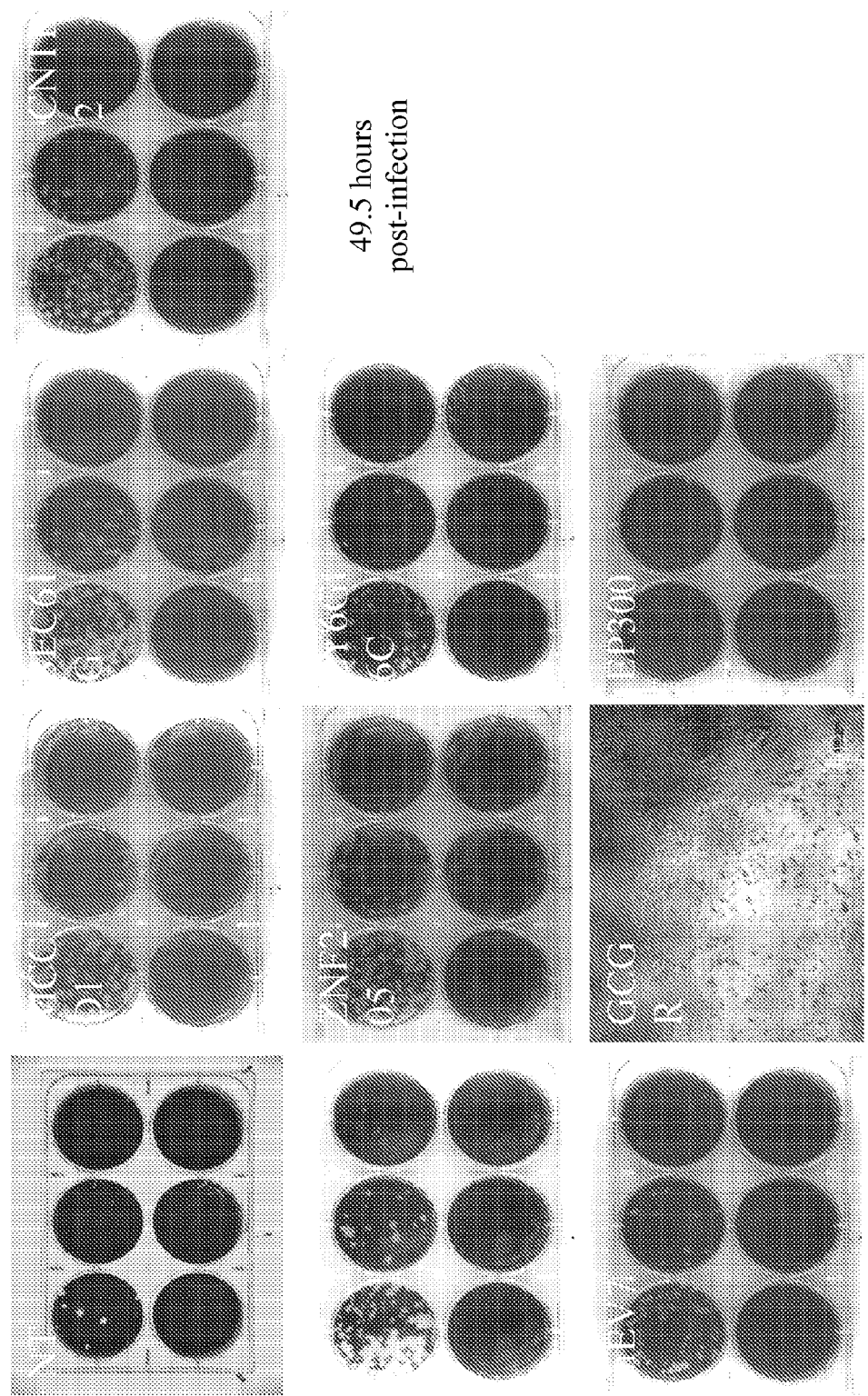
Figure 10B:
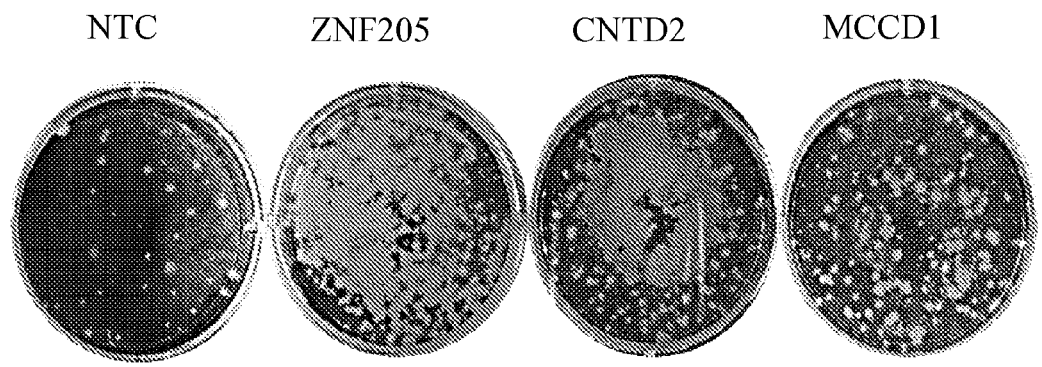
Figure 10C:
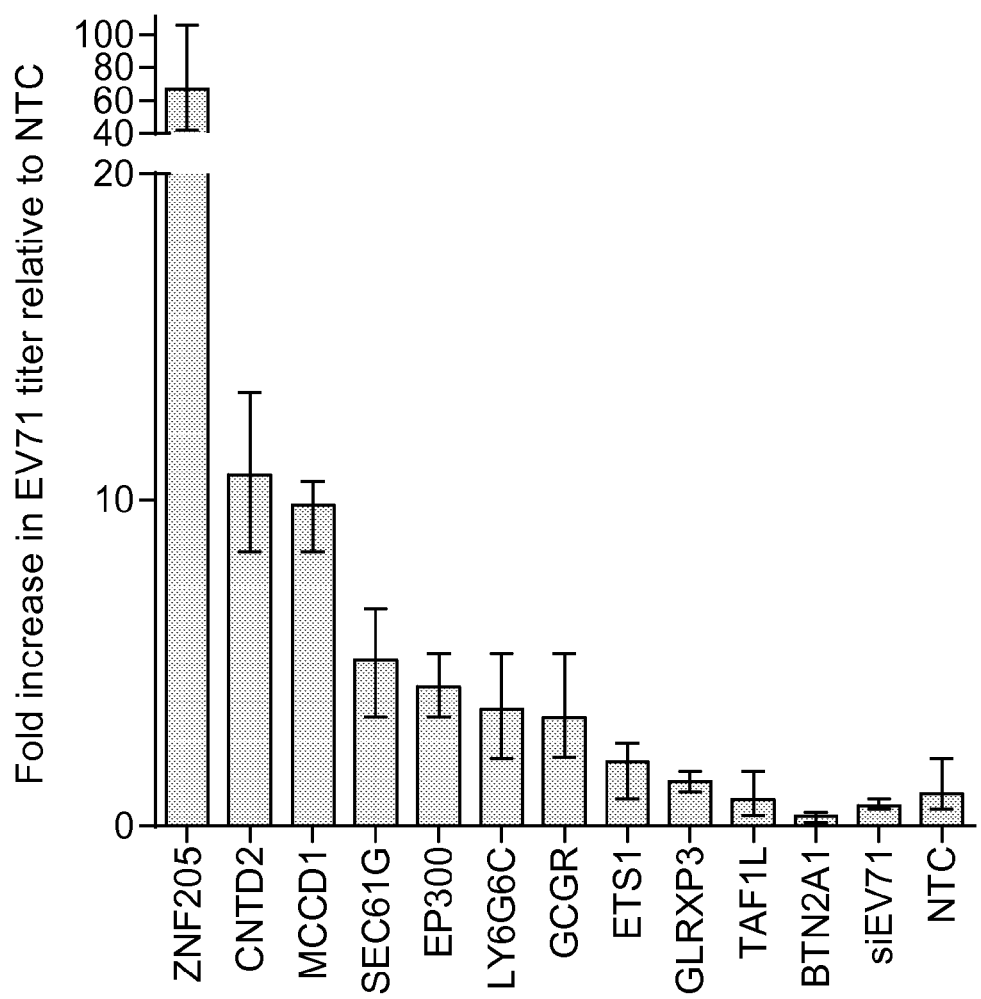

FIG. 10. (A) Effects of gene silencing on EV71 virus production. Vero cells were transfected with siRNA targeting one of several genes identified during the poliovirus RNAi screen. Following an appropriate period for gene silencing, EV71 was added to the culture. Subsequently, relative titers were assessed by examining cytopathic effects (CPE). (B) Plaque assay results demonstrating how silencing the three different genes (ZNF205, CNTD2, and MCCD1) affect EV71 titers. "RD cells"=rhabdomyosarcoma cells. (C) Bar graph quantitating the results from plaque assays. Experiments were performed in triplicate and incorporated a non-targeting control siRNA (NTC), and an siRNA targeting the EV71 genome (siEV71).

Table I. Provides a list of the 124 genes that increased poliovirus antigen and replication. Table provides gene names, KEGG conversion number, and Z-score values from the primary polio-specific ELISA.

Table II. Provides a list of greater than 100 genes that when silenced, greatly reduce poliovirus antigen and virus production.

Table III. Provides a list of the 68 genes (out of the 124 hits identified in Table I) that had two or more siRNA that induced an increase in poliovirus antigen and virus production. Table provides gene names as well as the number of siRNA that induced the phenotype.

Table IV. Provides a list of host-encoded miRNAs that greatly reduce poliovirus antigen and virus production.

Table V. List of genes, accession numbers, and siRNA sequences that were used to generate data in FIG. 8.

Table VI. Forty-nine gene combinations that enhance poliovirus production in an additive or synergistic fashion.

DETAILED DESCRIPTION OF ILLUSTRATIVE EMBODIMENTS

The present disclosure will now be described in connection with preferred embodiments. These embodiments are presented to aid in an understanding of the present disclosure and are not intended, and should not be construed, to limit the disclosure in any way. All alternatives, modifications and equivalents that may become apparent to those of ordinary skill upon reading this disclosure are included within the spirit and scope of the present disclosure.

With regard to gene designations, single genes have often been denoted by multiple symbols. For example, in the literature the Cyclophilin B gene encoding peptidylprolyl isomerase B has been denoted as PPIB and CYPB. In the context of this document gene symbols, whether they be human or non-human, may be designated by either upper-case or lower case letters. Neither the use of one particular symbol nor the adoption of lower or upper case symbols is intended to limit the scope of the gene in the context of these inventions. All gene identification numbers identified herein (GeneID) are derived from the National Center for Biotechnology Information "Entrez Gene" or KEGG web site unless identified otherwise.

As used herein, the term "gene" refers to a transcription unit and regulatory regions that are adjacent (e.g., located upstream and downstream), and operably linked, to the transcription unit. A transcription unit is a series of nucleotides that are transcribed into an RNA molecule. A transcription unit may include a coding region. A "coding region" is a nucleotide sequence that encodes an unprocessed preRNA (i.e., an RNA molecule that includes both exons and introns) that is subsequently processed to an mRNA. A transcription unit may encode a non-coding RNA. A non-coding RNA is an RNA molecule that is not translated into a protein. Examples of non-coding RNAs include microRNA. The boundaries of a transcription unit are generally determined by an initiation site at its 5' end and a transcription terminator at its 3' end. A "regulatory region" is a nucleotide sequence that regulates expression of a transcription unit to which it is operably linked. Nonlimiting examples of regulatory sequences include promoters, enhancers, transcription initiation sites, translation start sites, translation stop sites, transcription terminators, and poly(A) signals. A regulatory region located upstream of a transcription unit may be referred to as a 5' UTR, and a regulatory region located downstream of a transcription unit may be referred to as a 3' UTR. A regulatory region may be transcribed and be part of an unprocessed preRNA. The term "operably linked" refers to a juxtaposition of components such that they are in a relationship permitting them to function in their intended manner.

As used herein, "decreased expression of a coding region" and "increased expression of a coding region" refer to a change in the transcription of a coding region, a change in translation of an mRNA encoded by a coding region, or a change in the activity of a polypeptide encoded by the coding region.

In the context of this document the term "vaccine" refers to an agent, including but not limited to a peptide or modified peptide, a protein or modified protein, a live virus, a live attenuated virus, an inactivated or killed virus, a virus-like particle (VLP), or any combination thereof, that is used to stimulate the immune system of an animal or human in order to provide protection against e.g., an infectious agent. Vaccines frequently act by stimulating the production of an antibody, an antibody-like molecule, or a cellular immune response in the subject(s) that receive such treatments.

The term "virus production" can refer to production of a live virus, an attenuated virus, and/or a VLP. Production can occur by routine methods including 1) production in an organism (e.g., an egg), a cultured cell (e.g., Vero cells), or in vitro (e.g., via a cell lysate).

The term "cell line" refers to a clonal population of cells that are able to continue to divide and not undergo senescence.

The term "vaccine cell line" describes any cell, or modified cell or any cell lysate or modified cell lysate derived in part or in full from one or more cells, used to generate a vaccine. The cell(s) can be derived from any number of sources including mammalian (including but not limited to human, non-human primate, hamster, dog), avian (e.g., chicken, duck), insect, and more. Cell lysates used to generate vaccines can similarly be derived from any number of cell types. In some instances the term "host cell" and "vaccine cell line" are synonymous and include any cell that is 1) the target for infection by a pathogenic agent (e.g., a virus), 2) used for the production of a virus or a subunit of a vaccine (e.g., an immunogenic protein), and/or 3) used for the production of a biomolecule.

The terms "enhanced vaccine cell line", "enhanced cell line", "engineered vaccine cell line", or "engineered cell line" all refer to cell lines or cell lysates that have been modified by one or more means to modulate the expression or properties of one or more endogenously expressed genes so as to augment the production or properties of a vaccine or biomolecule.

As used herein, the term "control cell line" and "control cell" refers to a cell line that is genetically similar to an engineered cell line but has not been engineered in the same way. For instance, an engineered cell line may have decreased expression of a coding region selected from Table I when compared to a control cell line that is not engineered in the same way.

Methods that can be used to modulate gene expression include but are not limited to small interfering RNAs (siRNAs), small hairpin RNAs (shRNAs), antisense molecules, zinc finger nucleases, meganucleases, TAL (TALE) nucleases, triplexes, modified triplexes, small molecules, altered expression of open reading frames (ORFs) or cloned DNAs and more.

In the context of this document, the term "target" or "target gene" or "hit" refers to any gene, including protein-encoding genes and non-coding RNAs (e.g., a miRNA) that (when modulated) positively or negatively alters some aspect of virus or biomolecule production. Target genes include endogenous host genes, pathogen (e.g., viral) genes, and transgenes.

The term "modulates" or "modulation" refers to the alteration of the regulation, expression or activity of a gene. In general, it is understood by those in the field that the term "modulation" includes increasing the expression or activity of a gene, decreasing the expression or activity of a gene, as well as altering the specificity or function of a gene. Modulating the expression or activity of a gene can be achieved by a number of means including altering one or more of the following: 1) gene copy number, 2) transcription or translation of a gene, 3) the transcript stability or longevity, 4) the number of copies of an mRNA or miRNA, 5) the availability of a non-coding RNA or non-coding RNA target site, 6) the position or degree of post-translational modifications on a protein, 7) the activity of a protein, and other mechanisms. Modulation can result in a significant reduction in target gene activity (e.g., at least 5%, at least 10%, at least 20% or greater reduction) or an increase in target gene activity (e.g., at least 10%, at least 20%, or greater increase). Furthermore, it is understood by those in the field that modulation of one or more genes can subsequently lead to the modulation of multiple genes (e.g., miRNAs).

The term "microRNA" is used according to its ordinary and plain meaning and refers to a microRNA molecule found in eukaryotes that is involved in RNA-based gene regulation (see, e.g., Carrington et al., 2003, Science, 301: 336-338). Individual miRNAs have been identified and sequenced in different organisms, and have been named based on submission to the miRNA Registry (Griffiths-Jones, 2004, Nucl. Acids Res., 32(Suppl 1):D109-D111, and see miRBase.org). Names of miRNAs are provided herein and their sequences are readily available through miRBase-.org. Additionally, other miRNAs are known to those of skill in the art and can be readily implemented in embodiments described herein. The methods and compositions should not be limited to miRNAs identified in the application, as they are provided as examples, not necessarily as limitations of the embodiments described herein. An miRNA having an miRNA region that is less than 100% identical to a natural miRNA region may be referred to as a "mimic miRNA." Said molecules can be modified or unmodified.

The term "bioprocessing" or "bioproduction" refers to laboratory- and industrial-scale production of biological product (e.g., a biotherapeutic, a vaccine) in 1) a cell line, 2) a cell lysate, or 3) a model in vivo platform (e.g. an egg).

The term "picornavirus" refers to members of the family Picornaviridae. Examples of members of the family Picornaviridae include members of the genus Enterovirus. Examples of members of the genus Enterovirus includes Enterovirus species A. An example of an Enterovirus species A is Enterovirus 71, also referred to herein as EV71. Examples of members of the genus Enterovirus includes Enterovirus species C. An example of Enterovirus species C includes poliovirus. Examples of wild type virulent poliovirus strains include Mahoney, Brunhilde, MEF-1, and Saukett. Examples of attenuated polivirus strains include Sabin 1, Sabin 2, and Sabin 3. A poliovirus may be serotype 1 (e.g., Sabin 1, Mahoney, and Brunhilde), serotype 2 (e.g., Sabin 2 and MEF-1), or serotype 3 (e.g., Sabin 3 and Saukett). The term "picornavirus" is intended to include any of the current or future picornaviruses that can be used in vaccine production. These include any and all wild type strains, parental strains, attenuated strains (such as Sabin strains of poliovirus serotypes 1, 2, and 3), VLPs, any member of the family Picornaviridae other than the three known polioviruses, as well as current or future recombinant or engineered strains.

Conditions that are "suitable" for an event to occur, such as production of a virus, or "suitable" conditions are conditions that do not prevent such events from occurring. Thus, these conditions permit, enhance, facilitate, and/or are conducive to the event.

Enhancing Picornavirus Production

The present disclosure is directed to compositions and methods for generating vaccines. In a preferred application, the compositions and methods are directed toward generating polio vaccine. Through the use of the present disclosure, compositions and methods that relate to modified cell lines, cell lysates and/or in vivo systems (e.g., in ovo) that improve vaccine production can be envisioned Vaccines can be generated by a variety of means. In one instance, cells from any number of sources including but not limited to human, non-human primate, canine, and avian are first cultured in an appropriate environment (e.g., a cell or tissue culture plate or flask) to a desired density. Subsequently, viral seed stocks (e.g., Sabin 2 poliovirus) are added to the culture where they infect cells. Infected cells are then transferred to a bioreactor (e.g., a single use bioreactor) where the virus replicates and expands in number. After a suitable period of time, the cells and cell particulate are separated from newly released viral particles and additional steps (e.g., purification, deactivation, concentration) are performed to further prepare the material for use as a vaccine.

With regard to the growth of the virus, the host cell makes a critical contribution to viral replication. By example, host-encoded cell surface proteins are often used by viruses to gain entry into the cell (Ramos, I et. al. (2012) Front Microbiol. 3:117). Similarly, host compartments (e.g., endocytic vesicles) are frequently used by pathogens for transport to intra-cellular regions that have essential functions for pathogen-related gene processes (Karlas, A. et. al. (2010) Nature 463:818). Deletion of functions that are essential to pathogen propagation can have a detrimental effect on pathogen replication. Conversely, depletion of functions that negatively affect pathogen replication or over-expression of functions that are essential for pathogen propagation can, in some cases, greatly enhance the production of e.g., the virus (Kolokoltsov et. al. (2007) J. Virol. 81:7786).

While previous research has identified host-encoded gene knockdown and over-expression events that facilitate viral infection, it is well documented that these findings are often poorly replicated in even closely related systems. By example, several groups including Brass et al. (Science (2008) 319:921), and Konig et al. (Cell (2008) 135:49) have used RNAi technology to identify host-encoded genes that play a role in HIV replication. Over the course of these investigations, each group identified over two-hundred host-encoded genes that when modulated, altered one or more aspects of HIV replication. Yet when the gene hit lists generated by each group were compared, less than 10% of the genes were common to both data sets. Experts in the field attribute these results to subtle differences in a number of factors including the viral strains, the cell lines, and the assays employed in each of the studies. The inventors recognize the subtle importance of these findings and for that reason have focused their current studies on viruses and cell systems that are currently employed in vaccine production.

In one embodiment, provided herein is a list of protein-encoding genes that when modulated (individually or in combinations) enhance the production of picornavirus or picornavirus antigen, including, poliovirus or poliovirus antigen, in a cell, cell line, or cell lysate (Table I). Preferably, modulation of the gene(s) in the described list enhance the production of the Sabin-2 vaccine strain of poliovirus. More preferably, modulation of the gene(s) in the described list enhance the production of Sabin-1, Sabin 2, and/or Sabin 3 poliovirus or poliovirus antigen in a cell, cell line, or cell lysate that is used in poliovirus vaccine manufacturing.

TABLE I

List of genes that when silenced increase poliovirus antigen and virus production

| Gene name | Accession No. | Z-score |
| --- | --- | --- |
| SEC31L2 | NM_015490 | 5.35 |
| ZBTB12 | NM_181842 | 4.78 |
| UNQ3112 | NM_212555 | 4.73 |
| CETN1 | NM_004066 | 4.72 |
| LPAL2 | NR_028092 | 4.71 |
| ETS1 | NM_001143820 | 4.70 |
| HEPN1 | NM_001037558 | 4.67 |
| SNAP29 | NM_004782 | 4.61 |
| MLP | NM_023009.5 | 4.58 |
| KIAA1862 | NM_032534 | 4.58 |
| STK25 | NM_006374 | 4.52 |
| EDD1 | NM_015902 | 4.49 |
| OR10A7 | NM_001005280 | 4.48 |
| UNG | NM_003362 | 4.47 |
| GLRXL (also known as GLRXP3) | NM_001123388 | 4.41 |
| BCL9L | NM_182557 | 4.35 |
| VGLL2 | NM_153453 | 4.33 |
| IQGAP3 | NM_178229 | 4.27 |
| CHD5 | NM_015557 | 4.22 |
| RPL32 | NM_000994 | 4.22 |
| LOC164153 | NM_203412 | 4.20 |
| DKFZP434O047 | NM_015594 | 4.16 |
| ZFYVE19 | NM_001077268 | 4.15 |
| ACVR2B | NM_001106 | 4.13 |
| TREM5 | NM_174892 | 4.11 |
| CDR2 | NM_001802 | 4.10 |
| FLJ40121 | NM_001038704 | 4.05 |
| LOC201176 | NM_199282 | 4.02 |
| PKIG | NM_007066 | 3.99 |
| LOC389860 | NM_001015038 | 3.95 |
| CREB1 | NM_004379 | 3.94 |
| CHCHD7 | NM_001011667 | 3.91 |
| MAOA | NM_000240 | 3.91 |
| TUBB8 | NM_177987 | 3.89 |
| TMP21 | NM_006827 | 3.87 |
| BTN2A1 | NM_001197233 | 3.85 |
| LOC345778 | NM_001167741 | 3.85 |
| MGC52423 | NM_001164829 | 3.82 |
| SAST | XM_032034 | 3.80 |
| EFCBP2 | NM_019065 | 3.80 |
| STAU | NM_001037328 | 3.73 |
| RP1-93H18.5 | NM_001010919 | 3.69 |
| SLC39A14 | NM_001128431 | 3.63 |
| ITPK1 | NM_001142593 | 3.62 |
| LY6G6C | NM_025261 | 3.60 |
| MUC1 | NM_001018016 | 3.59 |
| LOC120824 | NM_001206625 | 3.58 |
| SIN3B | NM_015260 | 3.58 |
| NEDD9 | NM_001142393 | 3.56 |
| EP300 | NM_001429 | 3.55 |
| PDCD1LG2 | NM_025239 | 3.54 |
| SIGLEC5 | NM_003830 | 3.52 |
| TMSB4Y | NM_004202 | 3.52 |
| HRI | NM_001134335 | 3.52 |

TABLE I-continued

List of genes that when silenced increase poliovirus antigen and virus production

| Gene name | Accession No. | Z-score |
|---|---|---|
| MCCD1 (also known as LOC401250) | NM_001011700 | 3.51 |
| TAF1 | NM_004606 | 3.51 |
| MGC5352 | NM_001170543 | 3.50 |
| OR10H1 | NM_013940 | 3.48 |
| CNTD2 (also known as FLJ13265) | NM_024877 | 3.47 |
| MKRN2 | NM_014160 | 3.46 |
| TAF1L | NM_153809 | 3.46 |
| FOXD4L2 | NM_001099279 | 3.45 |
| MED31 | NM_016060 | 3.43 |
| C20ORF129 | NM_030919 | 3.43 |
| BET1L | NM_001098787 | 3.42 |
| FLJ00193 | NM_001080471 | 3.39 |
| SLC1A2 | NM_001195728 | 3.38 |
| ZNF135 | NM_001164527 | 3.35 |
| ZDHHC4 | NM_001134387 | 3.34 |
| COLEC11 | NM_024027 | 3.33 |
| OR4K15 | NM_001005486 | 3.33 |
| RENT1 | NM_002911 | 3.33 |
| LOC126917 | XM_375695 | 3.32 |
| KIAA0459 | NM_015207 | 3.31 |
| HR | NM_005144 | 3.31 |
| DSP | NM_004415 | 3.30 |
| SYT7 | NM_004200 | 3.28 |
| MELL1 | NM_033467 | 3.28 |
| GTF3C2 | NM_001035521 | 3.28 |
| VILL | NM_015873 | 3.27 |
| RNF20 | NM_019592 | 3.26 |
| MYO3B | NM_001083615 | 3.26 |
| CCNL2 | NM_001039577 | 3.26 |
| ANKRD12 | NM_001083625 | 3.25 |
| LILRA2 | NM_001130917 | 3.25 |
| KRTAP4-4 | NM_032524 | 3.25 |
| CCL24 | NM_002991 | 3.20 |
| SEC61G | NM_001012456 | 3.19 |
| JUND | NM_005354 | 3.19 |
| DPM2 | NM_003863 | 3.19 |
| SIRT4 | NM_012240 | 3.18 |
| CTAGE4 | NM_198495 | 3.17 |
| PRAMEF8 | NM_001012276 | 3.16 |
| BOLL | NM_033030 | 3.16 |
| ZNF206 | NM_032805 | 3.15 |
| UGCG | NM_003358 | 3.15 |
| YBX1 | NM_004559 | 3.14 |
| KRT3 | NM_057088 | 3.14 |
| CCL7 | NM_006273 | 3.14 |
| MANSC1 | NM_018050 | 3.13 |
| SEC61A1 | NM_013336 | 3.13 |
| MICB | NM_005931 | 3.13 |
| KPNA1 | NM_002264 | 3.12 |
| TFAP4 | NM_003223 | 3.12 |
| ARHGEF2 | NM_001162383 | 3.11 |
| SEMG1 | NM_003007 | 3.11 |
| SIK2 | NM_015191 | 3.11 |
| CCL16 | NM_004590 | 3.11 |
| RASSF4 | NM_032023 | 3.10 |
| MARCH3 | NM_178450 | 3.10 |
| DZIP1 | NM_014934 | 3.10 |
| FBXO42 | NM_018994 | 3.09 |
| GPR30 | NM_001039966 | 3.09 |
| SPATA13 | NM_001166271 | 3.09 |
| C20ORF177 | NM_022106 | 3.08 |
| FKBP14 | NM_017946 | 3.07 |
| IRS4 | NM_003604 | 3.05 |
| DTYMK | NM_001165031 | 3.04 |
| VDR | NM_001017536 | 3.03 |
| ZNF205 | NM_001042428 | 3.03 |
| GALNACT-2 | NM_018590 | 3.02 |
| PIAS2 | NM_004671 | 3.02 |
| BRMS1L | NM_032352 | 3.02 |
| CYP1A2 | NM_000761 | 3.01 |
| BRD4 | NM_014299 | 3.01 |
| SLC12A3 | NM_000339 | 3.00 |
| CELSR3 | NM_001407 | 2.53 |
| GCGR | NM_000160 | 2.83 |
| OPN3 | NM_014322 | 2.21 |
| PAK1 | NM_002576 | 2.95 |

The list includes genes that fall into multiple classes/families and functions including but not limited to kinases, proteases, ubiquitination, innate immunity, apoptosis, and more. As shown in the Examples, down-regulation of certain genes significantly enhances the production of viral proteins and/or the overall titer of live infectious picornavirus. At the same time, the screen used in this study also identified a collection of genes that, when silenced, reduced poliovirus replication (Table II, Examples). It is recognized that this latter class of genes represent a valuable collection of potential therapeutic targets for the treatment of polio and other viral diseases. This list is also valuable from the perspective of vaccine manufacturing in that over-expression of these genes should enhance picornavirus production.

TABLE II

List of genes that when silenced reduce poliovirus antigen and virus production

| Gene name | Accession number | Z-score |
|---|---|---|
| PTPN9 | NM_002833 | -2.7385 |
| TDP1 | NM_001008744 | -2.62421678 |
| GLRA1 | NM_000171 | -2.5816 |
| RAB7 | NM_004637 | -2.56473341 |
| KLF15 | NM_014079 | -2.56065162 |
| COPA | NM_001098398 | -2.54894774 |
| C9ORF123 | NM_033428 | -2.5480179 |
| RAN | NM_006325 | -2.51979459 |
| SOX2 | NM_003106 | -2.50782291 |
| ARL2 | NM_001199745 | -2.50310843 |
| SCAMP2 | NM_005697 | -2.49992908 |
| UBE2I | NM_003345 | -2.48383828 |
| RPS13 | NM_001017 | -2.47448119 |
| ASB14 | NM_001142733 | -2.465731 |
| DLEC1 | NM_007335 | -2.45854856 |
| KIF11 | NM_004523 | -2.44757255 |
| CHRDL1 | NM_001143981 | -2.43765162 |
| ARCN1 | NM_001142281 | -2.43253991 |
| RPL27 | NM_000988 | -2.43177109 |
| CCT8 | NM_006585 | -2.42916239 |
| FBXO24 | NM_001163499 | -2.42305456 |
| FABP2 | NM_000134 | -2.41676419 |
| FLNC | NM_001127487 | -2.4057734 |
| APOC1 | NM_001645 | -2.39426297 |
| TSTA3 | NM_003313 | -2.39391153 |
| OR4F15 | NM_001001674 | -2.39213505 |
| LSM11 | NM_173491 | -2.39060755 |
| CAGLP | NM_138705 | -2.36202792 |
| KISS1 | NM_002256 | -2.36122944 |
| SON | NM_032195 | -2.35523255 |
| PHC3 | NM_024947 | -2.34996112 |
| PSMD1 | NM_001191037 | -2.34541941 |
| STMN1 | NM_001145454 | -2.34328443 |
| FBXO5 | NM_001142522 | -2.34003556 |
| BCL2 | NM_000633 | -2.3380053 |
| RPL10L | NM_080746 | -2.33109113 |
| KRTAP9-4 | NM_033191 | -2.32159817 |
| NHP2L1 | NM_001003796 | -2.32069813 |
| RPL37A | NM_000998 | -2.31999381 |
| ARL5 | NM_001037174 | -2.31751988 |
| B3GALT1 | NM_020981 | -2.31702776 |
| WBSCR20C | NR_033323 | -2.31475549 |

TABLE II-continued

List of genes that when silenced reduce poliovirus antigen and virus production

| Gene name | Acc

TABLE II-continued

List of genes that when silenced reduce poliovirus antigen and virus production

| Gene name | Accession number | Z-score |
| --- | --- | --- |
| MS4A5 | NM_023945 | −2.09954455 |
| FLJ90575 | NM_153376 | −2.09576913 |
| NUDT2 | NM_001161 | −2.0936 |
| PSMA5 | NM_001199772 | −2.09227158 |
| IFNA16 | NM_002173 | −2.09196505 |
| C6ORF168 | NM_032511 | −2.09161864 |
| LOC200373 | NM_001029996 | −2.09127336 |
| LAX1 | NM_001136190 | −2.08983415 |
| MOX2 | NM_005924 | −2.08936807 |
| ZNF445 | NM_181489 | −2.08931855 |
| ZNF70 | NM_021916 | −2.08917296 |
| PPP1R15B | NM_032833 | −2.0870 |
| SNX1 | NM_001242933 | −2.08675257 |
| CCDC7 | NM_001026383 | −2.08292088 |
| PSMD11 | NM_002815 | −2.08251537 |
| NUP62 | NM_001193357 | −2.0823 |
| MGC4825 | NM_024122 | −2.08228284 |
| UNC13B | NM_006377 | −2.07996457 |
| ZNF403 | NM_024835 | −2.07959828 |
| CD1B | NM_001764 | −2.07677713 |
| KRTAP10-10 | NM_181688 | −2.07669081 |
| LIN28 | NM_024674 | −2.07497392 |
| SSTR4 | NM_001052 | −2.0732 |
| LILRA1 | NM_006863 | −2.07199264 |
| FLJ10379 | NM_018079 | −2.07189426 |
| IGSF3 | NM_001007237 | −2.07131291 |
| GRINA | NM_000837 | −2.0709 |
| VDAC2 | NM_001184783 | −2.0706 |
| UTP14C | NM_021645 | −2.06937615 |
| FLJ13615 | NM_025114 | −2.06826692 |
| TEX9 | NM_198524 | −2.06672242 |
| TAPBPL | NM_018009 | −2.06621575 |
| NUP85 | NM_024844 | −2.06390811 |
| LOC138046 | NM_173848 | −2.05981937 |
| GRASP | NM_181711 | −2.05795653 |
| DAAM2 | NM_001201427 | −2.05764456 |
| LR8 | NM_001101311 | −2.05695923 |
| FBXO33 | NM_203301 | −2.0561 |
| EPPB9 | NM_001243473 | −2.0554743 |
| MUC13 | NM_033049 | −2.05457618 |
| C6ORF80 | NM_015439 | −2.0540694 |
| CNKSR1 | NM_006314 | −2.05370393 |
| GGT1 | NM_001032364 | −2.05346804 |
| C21ORF7 | NM_020152 | −2.05203521 |
| ET | NM_001168319 | −2.05187728 |
| SERPINE1 | NM_000602 | −2.04966409 |
| SPEC1 | NM_001038707 | −2.04931329 |
| C7ORF9 | NM_022150 | −2.04784542 |
| FBXO41 | NM_001080410 | −2.04630167 |
| RPL30 | NM_000989 | −2.04587416 |
| BPY2 | NM_004678 | −2.04444691 |
| KIAA1441 | NM_020832 | −2.0437645 |
| RPL35A | NM_000996 | −2.04280134 |
| CD37 | NM_001040031 | −2.04198632 |
| PIK4CB | NM_001198773 | −2.0417 |
| RPS28 | NM_001031 | −2.0399029 |
| PIP5K1A | NM_001135636 | −2.0398 |
| ANXA10 | NM_007193 | −2.03941415 |
| AP2S1 | NM_004069 | −2.03839463 |
| OXER1 | NM_148962 | −2.0381 |
| PSMB3 | NM_002795 | −2.03807125 |
| THY28 | NM_001037304 | −2.03786908 |
| LRIG3 | NM_001136051 | −2.03703198 |
| CGB | NM_000737 | −2.03585165 |
| UNC13D | NM_199242 | −2.03574454 |
| OBFC1 | NM_024928 | −2.03545065 |
| WASPIP | NM_001077269 | −2.03521021 |
| ACP1 | NM_001040649 | −2.0350 |
| STRAP | NM_007178 | −2.03426288 |
| CDY1B | NM_001003894 | −2.03368024 |
| FLJ20422 | NM_017814 | −2.03350425 |
| FAU | NM_001997 | −2.03202082 |
| FLJ14624 | NM_001079669 | −2.03185235 |
| PDCL3 | NM_024065 | −2.03097313 |
| RLN3 | NM_080864 | −2.02980741 |
| ECHDC1 | NM_001002030 | −2.02944487 |
| FLJ46481 | XM_003118524 | −2.02884842 |
| RINT-1 | NM_021930 | −2.02877638 |
| KRTHA1 | NM_002277 | −2.02819748 |
| TJP2 | NM_001170414 | −2.0271 |
| LOC253982 | NM_181718 | −2.02604517 |
| PPRC1 | NM_015062 | −2.02577162 |
| ACTG1 | NM_001199954 | −2.02493498 |
| SHD | NM_020209 | −2.02492758 |
| RPS24 | NM_001026 | −2.02480869 |
| IL28B | NM_172139 | −2.02451469 |
| PSMD6 | NM_014814 | −2.02447849 |
| LOC51058 | NM_015911 | −2.0225011 |
| LOC154907 | NM_001024607 | −2.02248766 |
| KCNA2 | NM_001204269 | −2.0224 |
| LOC92235 | XM_043739 | −2.022006 |
| MGC12197 | NM_016625 | −2.01939695 |
| LOC284123 | NM_203392 | −2.01860474 |
| PSMA3 | NM_002788 | −2.01815147 |
| FBXO7 | NM_001033024 | −2.01796185 |
| SFI1 | NM_001007467 | −2.0178263 |
| RASGRP3 | NM_001139488 | −2.01736034 |
| COPZ1 | NM_016057 | −2.0171775 |
| MGC42090 | NM_152774 | −2.01709049 |
| KATNAL2 | NM_031303 | −2.01581373 |
| SLC5A9 | NM_001011547 | −2.01549479 |
| MAP7 | NM_001198608 | −2.01483677 |
| MGC10820 | NM_032648 | −2.01452268 |
| SFRS14 | NM_001017392 | −2.01368004 |
| KIAA1912 | NM_001080433 | −2.01364824 |
| URB1 | NM_014825 | −2.01325122 |
| SYCN | NM_001080468 | −2.01317113 |
| ABI1 | NM_001012750 | −2.01297548 |
| C10ORF119 | NM_001256378 | −2.01273666 |
| MGC3040 | NM_001136469 | −2.01269528 |
| MYO1F | NM_012335 | −2.01201535 |
| EPM2A | NM_001018041 | −2.0108 |
| FLJ31052 | NM_001002901 | −2.01052556 |
| FLJ32830 | NM_152781 | −2.01003276 |
| ZNF499 | NM_032792 | −2.00957103 |
| CHRNA2 | NM_000742 | −2.0085 |
| KIAA0431 | NM_015251 | −2.00569093 |
| TIMM13 | NM_012458 | −2.00545588 |
| PRKWNK2 | NM_006648 | −2.0032 |
| RIPK2 | NM_003821 | −2.0027 |
| SSTR5 | NM_001053 | −2.0025 |
| OR2AG1 | NM_001004489 | −2.002257 |
| RPS27A | NM_002954 | −2.00143551 |
| TNFRSF6B | NM_003823 | −2.00134172 |

The mechanisms by which picornavirus production is enhanced are likely to be diverse. In some cases, genes identified in the screen have direct negative interactions with one or more components of the virus. For instance, the host gene product may be a direct mediator of the cell's innate immunity and therefore have anti-viral properties by e.g., detecting the viral genome and subsequently inducing an apoptotic state. In other instances, the gene's action may be indirect, where modulation of the gene product positively affects viral replication by modifying a pathway, a compartment, or a cellular state that the virus relies upon for e.g., replication. For instance, it is conceivable that particular modulation events enhance a host-protein post-translational modification and in doing so, positively augment one or more host cell secretion pathways that are essential for viral replication. Alternatively, modulation of one or more of the genes may increase cell viability, thereby increasing the number of cells capable of supporting viral replication. In yet another scenario, modulation of one or more genes may lock the cell into a stage of the cell cycle that is more conducive to viral growth. In these instances, the inventors foresee that the benefits of the invention may not be limited to poliovirus vaccine production but may extend to other picornaviruses or biomolecules (e.g., therapeutic antibodies).

Modulation of the genes identified herein can be achieved by multiple methods including techniques that manipulate genomic DNA, messenger and/or non-coding RNA and/or proteins. As such, the technologies or mechanisms that can be employed to modulate a gene of interest include but are not limited to 1) technologies and reagents that target genomic DNA to result in an edited genome (e.g., homologous recombination to introduce a mutation such as a deletion into a gene, zinc finger nucleases, meganucleases, transcription activator-like effectors (e.g., TALENs), triplexes, mediators of epigenetic modification, and CRISPR and rAAV technologies), 2) technologies and reagents that target RNA (e.g. agents that act through the RNAi pathway, antisense technologies, ribozyme technologies), and 3) technologies that target proteins (e.g., small molecules, aptamers, peptides, auxin- or FKBP-mediated destabilizing domains, antibodies).

In one embodiment for targeting DNA, gene modulation is achieved using zinc finger nucleases (ZFNs). Synthetic ZFNs are composed of a custom designed zinc finger binding domain fused with e.g. a FokI DNA cleavage domain. As these reagents can be designed/engineered for editing the genome of a cell, including, but not limited to, knock out or knock in gene expression, in a wide range of organisms, they are considered one of the standards for developing stable engineered cell lines with desired traits. Meganucleases, triplexes, CRISPR, and recombinant adeno-associated viruses have similarly been used for genome engineering in a wide array of cell types and are viable alternatives to ZFNs. The described reagents can be used to target promoters, protein-encoding regions (exons), introns, 5' and 3' UTRs, and more.

Another embodiment for modulating gene function utilizes the cell's endogenous RNA interference (RNAi) pathways to target cellular messenger RNA. In this approach, gene targeting reagents include small interfering RNAs (siRNA) as well as microRNAs (miRNA). These reagents can incorporate a wide range of chemical modifications, levels of complementarity to the target transcript of interest, and designs (see U.S. Pat. No. 8,188,060) to enhance stability, cellular delivery, specificity, and functionality. In addition, such reagents can be designed to target diverse regions of a gene (including the 5' UTR, the open reading frame, the 3' UTR of the mRNA), or (in some cases) the promoter/enhancer regions of the genomic DNA encoding the gene of interest. Gene modulation (e.g., knockdown) can be achieved by introducing (into a cell) a single siRNA or miRNA or multiple siRNAs or miRNAs (i.e., pools) targeting different regions of the same mRNA transcript. Synthetic siRNA/miRNA delivery can be achieved by any number of methods including but not limited to 1) self-delivery (US Patent Application No 2009/0280567A1), 2) lipid-mediated delivery, 3) electroporation, or 4) vector/plasmid-based expression systems. An introduced RNA molecule may be referred to as an exogenous nucleotide sequence or polynucleotide.

Another gene targeting reagent that uses RNAi pathways includes small hairpin RNA, also referred to as shRNA. shRNAs delivered to cells via e.g., expression constructs (e.g., plasmids, lentiviruses) have the ability to provide long term gene knockdown in a constitutive or regulated manner, depending upon the type of promoter employed. In one preferred embodiment, the genome of a lentiviral particle is modified to include one or more shRNA expression cassettes that target a gene (or genes) of interest. Such lentiviruses can infect a cell intended for vaccine production, stably integrate their viral genome into the host genome, and express the shRNA(s) in a 1) constitutive, 2) regulated, or (in the case where multiple shRNA are being expressed) constitutive and regulated fashion. In this way, cell lines having enhanced picornavirus production capabilities can be created. It is worth noting, that approaches that use siRNA or shRNA have the added benefit in that they can be designed to target individual variants of a single gene or multiple closely related gene family members. In this way, individual reagents can be used to modulate larger collections of targets having similar or redundant functions or sequence motifs. The skilled person will recognize that lentiviral constructs can also incorporate cloned DNA, or ORF expression constructs.

In another embodiment, modulation takes place at the protein level. By example, knockdown of gene function at the protein level can be achieved by a number of means including but not limited to targeting the protein with a small molecule, a peptide, an aptamer, destabilizing domains, or other methods that can e.g., down-regulate the activity or enhance the rate of degradation of a gene product. In one preferred instance, a small molecule that binds e.g. an active site and inhibits the function of a target protein can be added to e.g., the cell culture media and thereby introduced into the cell. Alternatively, target protein function can be modulated by introducing e.g. a peptide into a cell that (for instance) prevents protein-protein interactions (see for instance, Shangary et. al., (2009) Annual Review of Pharmacology and Toxicology 49:223). Such peptides can be introduced into a cell by transfection or electroporation, or introduced via an expression construct. Alternatively, peptides can be introduced into cells by 1) adding (e.g., through conjugation) one or more moieties that facilitate cellular delivery, or 2) supercharging molecules to enhance self-delivery (Cronican, J. J. et al (2010) ACS Chem. Biol. 5(8):747-52). Techniques for expressing a peptide include, but are not limited to 1) fusion of the peptide to a scaffold, or 2) attachment of a signal sequence, to stabilize or direct the peptide to a position or compartment of interest, respectively.

While genes provided herein were identified in a screen designed to identify gene knockdown events that enhance Sabin-2 capsid antigen and poliovirus production, work presented in the Examples section demonstrate that modulation of these targets also enhances the production of other serotypes of poliovirus (e.g., Sabin 1, Sabin 3), and of Enterovirus 71. This is of particular importance from the perspective of vaccine manufacturers since current poliovirus vaccines include all three serotypes (e.g. Sabin 1, Sabin 2, and Sabin 3, or wild type strains of each of the three serotypes). For this reason, an additional embodiment includes a list of genes that when modulated enhance the production of picornaviruses or picornavirus antigens other than Sabin 2 poliovirus or Sabin 2 poliovirus antigen, including but not limited to viruses and antigens derived from Sabin 1, Sabin 3, other poliovirus strains, and enterovirus 71.

The original screen for genes that enhanced poliovirus production took place in a HEp-2C cell line. HEp-2C cells are human in origin and for this reason, the original screen identified human genes that when modulated, enhance poliovirus production. As described in the Examples section below, validation studies utilized Vero cells which are derived from the African Green Monkey kidney. As hits identified in the primary screen also increase poliovirus titers in Vero cells, an additional embodiment includes a list of genes that are orthologs of those identified in the primary screen (Table I). Such orthologs can be modulated in human or non-human cells, cell lines, or cell lysates to increase picornavirus or picornavirus antigen production, including poliovirus or poliovirus antigen production. Examples of cells and cell lines useful in the methods described herein include primate cells that are known to support replication of picornavirus. Such cells can be human, chimpanzee, and monkey cells. Specific examples include, but are not limited to, WI-38, MRC-5, HEK293, PERC6, HeLa, and African Green Monkey kidney cells, such as Vero cells.

Separately, the inventors recognize that the list of genes identified in Table I are also potential drug targets to increase polio virus replication. For this reason, in a separate embodiment, genes listed in Table I can be modulated to increase picornavirus replication, and thereby enhance the production of picornavirus, including poliovirus. Examples of small molecules that may be used to increase replication of poliovirus include, but are not limited to, SU1489, PD98059, Retinoic acid, curcumin, ly294002, DL-TBOA (DL-threo-β-Benzyloxyaspartic acid), and DL-threo-β-Hydroxyaspartic acid.

Another embodiment includes knockout animals (e.g., knockout mice) having one or more of the genes identified in the Tables below modified to enhance or diminish picornavirus replication.

Another embodiment includes a list of microRNAs (miRNAs) that enhance picornavirus antigen and picornavirus production. As shown in the Examples section, a microRNA (miRNA) mimic screen was performed to identify miRNAs that (when upregulated) enhance the production of poliovirus. The miRNA mimic screen identified multiple, host-encoded miRNAs that facilitated Sabin 2 poliovirus production. The proviral miRNAs identified were miR-520e, miR-1256, miR-520d-3p, miR-513a-5p, miR-519c-3p, miR-1270-2, miR-3187, miR-5763p, miR-22, miR-520c-3p, and miR-9. miRNAs miR-520e, miR-1256, miR-520d-3p, miR-513a-5p, and miR-519c-3p, increase poliovirus antigen and virus production by two- to four-fold compared to a control cell. miRNAs miR-1270-2, miR-3187, miR-5763p, miR-22, miR-520c-3p, and miR-9 increase live poliovirus production by four- to twelve-fold. These miRNAs can be modulated individually, in combination with other miRNAs, or in combination with one or more protein-encoding genes to boost picornavirus or picornavirus antigen production. As this collection of miRNAs boost poliovirus production, the addition of a microRNA inhibitor is expected to greatly reduce picornavirus production in cells where the endogenous miRNA is present. As such, another embodiment includes a list of microRNA inhibitors designed to target the list of pro-viral miRNAs that can be used as potential therapeutic agents against polio.

miRNA inhibitors (also referred to in the art as anti-miRs, antagomirs, and/or blockmirs) are engineered nucleotide sequences that, when introduced into a cell, silence endogenous miRNAs. The production, identification, and use of miRNA inhibitors is known to the person skilled in the art and is routine. Exemplary designs of miRNA inhibitors include but are not limited to those described by 1) Hutvagner et al., 2004, PLoS Biol., 2:E98, 2) Meister et al., 2004, RNA 10:544-550, 3) and Vermeulen et al., 2007, RNA, 13:723-730.

Importantly, the screen also identified miRNA mimics that decrease poliovirus antigen and/or virus production (see Examples and Table IV). As such, another embodiment includes the list of antiviral miRNAs as potential therapeutic agents to treat polio infection. Moreover, inhibition of these antiviral miRNAs (by, for instance, a miRNA inhibitor) is predicted to increase picornavirus antigen and virus production. As such, another embodiment includes the list of inhibitors targeting the list of antiviral miRNAs to facilitate picornavirus antigen and virus production. In cases where a miRNA inhibitor(s) could be implemented (for therapeutic or vaccine production) a variety of designs can be employed including but not limited to modified and unmodified single site linear molecules, modified or unmodified molecules that incorporate hairpin structures, and modified or unmodified designs that have concatemers of full or partial miRNA target sites.

The original screen for miRNAs that enhanced poliovirus production took place in a HEp-2C cell line. HEp-2C cells are human in origin and for this reason, the original screen identified human miRNAs that when modulated, enhance poliovirus production. As miRNAs found in one species often exist in other species in identical or closely related forms, an additional embodiment includes a list of miRNAs that are orthologs of those identified in the primary screen that can be modulated in human or non-human cells, cell lines, or cell lysates to increase picornavirus or picornavirus antigen production.

Another embodiment provides a cell line (human or non-human) that has one or more genes identified in the Examples (or orthologs to genes identified in the Examples) modified to enhance picornavirus or picornavirus antigen production. A cell line includes i) a modification of at least one coding region present in a gene described in Table I (or an ortholog thereof) so that there is a decrease in expression of the coding region, ii) a modification of at least one coding region present in a gene described in Table II (or an ortholog thereof) so that there is an increase in expression of the coding region, iii) increased expression of at least one miRNA selected from miR-520e, miR-1256, miR-520d-3p, miR-513a-5p, miR-519c-3p, miR-1270-2, miR-3187, miR-5763p, miR-22, miR-520c-3p, and miR-9, iv) an inhibitor that targets an antiviral miRNA described in Table IV, or v) a combination thereof. The modification of at least one coding region present in a gene described in Table I may be achieved through an alteration of the gene in the genome of the cell, or the presence of siRNA, shRNA, or antisense RNA in the cell. An alteration of a gene includes, but is not limited to, a mutation in the coding region or a regulatory region operably linked to the coding region. In one embodiment, the modified genes enhance Sabin 1, Sabin 2, and/or Sabin 3 production or production of wild type poliovirus strains used to produce IPV. In one embodiment, the modified genes enhance EV71 production. Preferably, the cell line and the poliovirus or polio antigen are employed in poliovirus vaccine production. The inventors perceive that the cell lines can be eukaryotic or engineered prokaryotic. Alternatively, the cells can be synthetic (i.e., artificially generated) in nature (Gibson et al. (2010) Science 329:52-56). In the case where the cells are eukaryotic or modified eukaryotic cells, said cells may be primary cells, continuous cells, immortalized cell (cell lines), or stem cells. Cells may be derived from human, non-human primates, mouse, rat, hamster, insect, and more. In one embodiment, the cells may be HEp-2C or a derivative thereof. In one embodiment, the cells may be Vero or a derivative thereof.

Another embodiment provides a cell lysate (human or non-human) that is derived from a cell line described herein. For instance, in one embodiment the cell lysate has one or more genes identified in the Examples (or orthologs to genes identified in the Examples) modified to enhance virus or viral antigen production. Preferably, the modified genes enhance Sabin 1, Sabin 2, and/or Sabin 3 virus or virus antigen production or production of wild type poliovirus strains used to produce IPV. Preferably, the cell lysates are employed in poliovirus vaccine production.

In another embodiment, the timing of target gene modulation can vary. In some cases it is envisioned that gene modulation may occur prior to picornavirus infection. For instance, if the gene target of choice locks the cell in a particular phase of the cell cycle that is highly productive for picornavirus replication or picornavirus antigen production, initiating gene modulation prior to viral infection may be beneficial. In other cases, it may be beneficial for picornavirus infection/replication or antigen production to be initiated prior to modulating the target gene of interest. For instance, if a particular host gene modulation event is essential at the later stages of viral replication or antigen production, but deleterious at the early stages, the inventors envision that gene modulation would be initiated after infection. In cases where two or more gene modulation events are required for optimized picornavirus or picornavirus antigen production, some of the genes may be modified before viral infection while others are modified after viral infection. Regardless of the timing of gene modulation, multiple methods (including, for instance, applications of shRNA in conjunction with regulatable (e.g., Tet-sensitive) promoter) can be employed to time the expression of gene modulation.

The pathway analysis studies performed on validated hits from the poliovirus screen identified genes that reside in the same pathway. Simultaneously, these studies also identified genes that reside in non-overlapping or unrelated pathways. In some instances, targeting two or more genes in a single pathway may provide additive or synergistic effects. In other instances, targeting two or more genes from unrelated pathways may significantly increase viral protein and/or virus production beyond what is achieved by modulation of any single gene (or pathway). Furthermore, modulating combinations of genes, some residing in the same pathway while others residing in unrelated pathways, can enhance virus and/or virus protein production. For this reason, in a separate embodiment two or more genes identified herein may be modulated to provide additive or synergistic effects on picornavirus or picornavirus antigen production. In such cases, any of the methods/technologies described above or employed by life scientists currently or in the future can be employed to modulate the two or more genes.

It should be noted that in the course of the screen it was observed that knockdown of certain host-encoded genes led to a decrease in polio virus replication (Table II). As such, in one embodiment, the inventors envision that over-expression of one or more of the genes listed in Table II can also enhance picornavirus or picornavirus antigen production. Over-expression of the genes listed in Table II can be achieved by a variety of methods including, but not limited to increasing gene copy number (i.e., introducing a cloned DNA or ORF expression construct), increasing promoter strength, altering epigenetic modifications, reducing mRNA degradation, enhancing protein function, or transfecting an mRNA, protein, protein domain, or peptide into the cell. Importantly, over-expression of any gene(s) listed in Table II can be done while simultaneously down-regulating one or more genes listed in Table I.

In a separate embodiment, the invention provides a method of producing picornavirus vaccine, such as poliovirus vaccine, in which cells or cell lysates having one or more genes or gene products modulated, are employed.

Separately, the inventors recognize that the list of genes identified in Table II are also potential therapeutic drug targets to fight picornavirus infection, including polio virus infection. For this reason, in a separate embodiment, genes listed in Table II can be modulated to reduce picornavirus replication, and thereby reduce the infection and the symptoms associated with picornavirus infection. Targeting of the genes in Table II can be achieved by a wide range of methods including small molecules, RNAi technologies, ribozymes (and more) using art-recognized delivery technologies.

Examples of small molecules that may be used to inhibit replication of poliovirus include, but are not limited to, Riluzole hydrochloride, Ceftriaxone disodium salt hemi (heptahydrate), pasireotide, lanreotide, octreotide, ABT-089, ABT 418, isoflurane, mecamylamine, succinylcholine, rocuronium, doxacurium, mivacurium, pipecuronium, rapacuronium, metocurine, atracurium, cisatracurium, acetylcholine, nicotine, D-tubocurarine, arecoline, enflurane, pancuronium, vecuronium, drotrecogin alfa, octreotide, tafluprost, travoprost, isopropyl unoprostone, bimatoprost, latanoprost, digoxin, omeprazole, ethacrynic acid, perphenazine, hexa-D-arginine, nona-D-arginine amide, dextromethorphan/guaifenesin, morphine/dextromethorphan, neramexane, bicifadine, delucemine, CR 2249, besonprodil, UK-240455, ketamine, felbamate, memantine, orphenadrine, cycloserine, N-(2-indanyl)glycinamide, dextromethorphan, brompheniramine/dextromethorphan/pseudoephedrine, chlorpheniramine/dextromethorphan/phenylephrine, carbinoxamine/dextromethorphan/pseudoephedrine, dextromethorphan/promethazine, 1-aminocyclopropane-1-carboxylic acid, elsamitrucin, T 0128, CT-2106, BN 80927, tafluposide, TAS-103, beta-lapachone, irinotecan, topotecan, 9-amino-20-camptothecin, rubitecan, gimatecan, karenitecin, oblimersen, (−)-gossypol, calcipotriene, vitamin D2, ILX-23-7553, alendronate/cholecalciferol, 2-(3-hydroxypropoxy)calcitriol, betamethasone dipropionate/calcipotriene, paricalcitol, doxercalciferol, cholecalciferol, 1-alpha, 25-dihydroxy vitamin D3, N-butyldeoxygalactonojirimycin, N-butyldeoxynojirimycin, riluzole, HuHMFG1, ladostigil, 1-ethylphenoxathiin 10,10-dioxide, moclobemide, dextroamphetamine, procainamide, tranylcypromine, phenelzine, iproniazid, isocarboxazid, benzphetamine, N-(2-indanyl)glycinamide Also provided herein is a kit that includes an engineered cell line described herein. In one embodiment, cells of the engineered cell line may be used as a host cell for infection by at least one picornavirus. In one embodiment, cells of the engineered cell line include at least one picornavirus. The cells may be used for production of virus. The engineered cell line may be present in a suitable packaging material in an amount sufficient for at least one use. Optionally, other reagents such as medium may be included. Instructions for use of the engineered cell line may also be included.

As used herein, the phrase "packaging material" refers to one or more physical structures used to house the contents of the kit. The packaging material is constructed by known methods, preferably to provide a sterile, contaminant-free environment, and may include a container, such as a tube, bottle, vial, syringe, or other suitable container means. The packaging material has a label which indicates how the engineered cell line can be used.

ILLUSTRATIVE EMBODIMENTS

Embodiment 1

An engineered cell line, wherein cells of the engineered cell line comprise decreased expression of a coding region selected from Table I compared to a control cell line, wherein the coding region is selected from ZNF205, CNTD2, SEC61G, ETS1, TAF1L, MCCD1, LY6G6C, BTN2A1, GLXP3, GCGR, EP300.

Embodiment 2

An engineered cell line, wherein cells of the engineered cell line comprise decreased expression of a coding region selected from Table I compared to a control cell line

Embodiment 3

The engineered cell line of embodiment 1 or 2 wherein the decrease is at least 5% compared to the control cell line.

Embodiment 4

The engineered cell line of embodiment 1 or 2 wherein the decrease in expression is determined by measuring the amount in the cells of polypeptide or mRNA encoded by the coding region.

Embodiment 5

The engineered cell line of embodiment 1 or 2 wherein the cells comprise a mutation in the coding region or in a regulatory region operably linked to the coding region.

Embodiment 6

The engineered cell line of embodiment 1 or 2 wherein the cells comprise an exogenous polynucleotide that decreases the expression of the coding region.

Embodiment 7

The engineered cell line of embodiment 5 wherein the exogenous polynucleotide is an RNA polynucleotide.

Embodiment 8

The engineered cell line of embodiment 7 wherein the RNA polynucleotide is a siRNA, a shRNA, or an antisense polynucleotide.

Embodiment 9

The engineered cell line of embodiment 1 or 2 wherein the cells comprise an edited genome that results in the decreased expression.

Embodiment 10

The engineered cell line of embodiment 9 wherein the genome is edited by a zinc finger nuclease, a meganuclease, or a transcription activator-like effector.

Embodiment 11

The engineered cell line of embodiment 1 or 2 wherein the cells further comprise decreased expression of at least one additional coding region selected from Table I, increased expression of an miRNA selected from miR-520e, miR-1256, miR-520d-3p, miR-513a-5p, miR-519c-3p, miR-1270-2, miR-3187, miR-5763p, miR-22, miR-520c-3p, and miR-9 compared to a control cell line, decreased expression of an miRNA selected from Table IV, or a combination thereof.

Embodiment 12

The engineered cell line of embodiment 11 wherein the cells comprise decreased expression of at least five coding regions selected from Table I.

Embodiment 13

The engineered cell line of embodiment 1 or 2 wherein the cells further comprise decreased expression of a combination of at least 2 coding regions, wherein the combinations of coding regions are selected from Table VI.

Embodiment 14

An engineered cell line, wherein cells of the engineered cell line comprise increased expression of a coding region selected from Table II compared to a control cell line.

Embodiment 15

The engineered cell line of embodiment 14 wherein the increase in expression is determined by measuring the amount in the cells of polypeptide or mRNA encoded by the coding region.

Embodiment 16

The engineered cell line of embodiment 14 wherein the cells further comprise increased expression of at least one additional coding region selected from Table II, decreased expression of an miRNA selected from miR-520e, miR-1256, miR-520d-3p, miR-513a-5p, miR-519c-3p, miR-1270-2, miR-3187, miR-5763p, miR-22, miR-520c-3p, and miR-9 compared to a control cell line, decreased expression of an miRNA selected from Table IV, or a combination thereof.

Embodiment 17

The engineered cell line of embodiment 14 wherein the cells comprise increased expression of at least five coding regions selected from Table II.

Embodiment 18

The engineered cell line of embodiment 14 wherein the increase is at least 5% compared to the control cell line.

Embodiment 19

An engineered cell line, wherein cells of the engineered cell line comprise increased expression of an miRNA selected from miR-520e, miR-1256, miR-520d-3p, miR-513a-5p, miR-519c-3p, miR-1270-2, miR-3187, miR-5763p, miR-22, miR-520c-3p, and miR-9 compared to a control cell line.

Embodiment 20

The engineered cell line of embodiment 19 wherein the cells comprise an miRNA mimic that behaves like one of the endogenous miRNAs.

Embodiment 21

The engineered cell line of embodiment 1 wherein the cells further comprise increased expression of at least two miRNAs. 9

Embodiment 22

The engineered cell line of embodiment 19 wherein the increase is at least 5% compared to the control cell line.

Embodiment 23

An engineered cell line, wherein cells of the engineered cell line comprise decreased expression of an endogenous miRNA selected from Table IV compared to a control cell line.

Embodiment 24

The engineered cell line of embodiment 23 wherein the cells comprise a mutation in the coding region encoding the endogenous miRNA or in a regulatory region operably linked to the coding region.

Embodiment 25

The engineered cell line of embodiment 23 wherein the cells comprise an miRNA inhibitor that inhibits activity of the endogenous miRNA.

Embodiment 26

The engineered cell line of embodiment 1, 2, 14, 19, or 23 wherein the cells comprise a picornavirus.

Embodiment 27

The engineered cell line of embodiment 26 wherein the picornavirus is a poliovirus

Embodiment 28

The engineered cell line of embodiment 27 wherein the poliovirus is chosen from either Sabin 1, Sabin 2, or Sabin 3.

Embodiment 29

The engineered cell line of embodiment 27 wherein the poliovirus is selected from Mahoney or Brunhilde.

Embodiment 30

The engineered cell line of embodiment 27 wherein the poliovirus is MEF-1.

Embodiment 31

The engineered cell line of embodiment 27 wherein the poliovirus is Saukett.

Embodiment 32

The engineered cell line of embodiment 28 wherein cells of the cell line comprise two or three polioviruses.

Embodiment 33

The engineered cell line of embodiment 26 wherein the picornavirus is enterovirus 71.

Embodiment 35

The engineered cell line of embodiment 1, 2, 14, 19, or 23 wherein the cell line is a mammalian cell line, an avian cell line, or an insect cell line.

Embodiment 36

The engineered cell line of embodiment 35 wherein the mammalian cell line is selected from a human cell line, a non-human primate cell line, a canine cell line, or a hamster cell line

Embodiment 37

The engineered cell line of embodiment 36 wherein the mammalian cell line is HEp-2 or Vero P.

Embodiment 38

The engineered cell line of embodiment 35 wherein the avian cell line is a chicken cell line, or a duck cell line.

Embodiment 39

The engineered cell line of embodiment 19 or embodiment 23 wherein the change in expression is determined by measuring the amount in the cells of the miRNA.

Embodiment 40

A lysate of the engineered cell line of embodiment 1, 2, 14, 19, or 23.

Embodiment 41

A method for producing a virus comprising: providing the engineered cell line of embodiment 1, 2, 14, 19, or 23 wherein cells of the cell line comprise a virus; incubating the engineered cell line under conditions suitable for the production of the virus by the cells; and harvesting the virus produced by the cells.

Embodiment 42

A method for producing a virus comprising: providing a cell line wherein cells of the cell line comprise a virus; incubating the cell line under conditions suitable for the production of the virus by the cells, wherein the medium comprises an RNA polynucleotide that inhibits expression of a coding region selected from Table I; and harvesting the virus produced by the cells.

Embodiment 43

The cell line of embodiment 42 wherein the RNA polynucleotide is a siRNA, a shRNA, or an antisense polynucleotide, an miRNA selected from miR-520e, miR-1256, miR- 520d-3p, miR-513a-5p, miR-519c-3p, miR-1270-2, miR-3187, miR-5763p, miR-22, miR-520c-3p, and miR-9, an mRNA inhibitor that inhibits activity of an endogenous miRNA selected from Table IV, or a combination thereof.

Embodiment 44

A method for producing a virus comprising: providing a cell line wherein cells of the cell line comprise a virus, and wherein the cells comprise an edited genome that results in decreased expression of a coding region selected from Table I; incubating the cell line under conditions suitable for the production of the virus by the cells; and harvesting the virus produced by the cells.

Embodiment 45

The engineered cell line of embodiment 43 wherein the genome is edited by a zinc finger nuclease, a meganuclease, or a transcription activator-like effector.

Embodiment 46

A method for producing a virus comprising: providing a cell line wherein cells of the cell line comprise a virus; incubating the cell line under conditions suitable for the production of the virus by the cells, wherein the medium comprises a small molecule that inhibits expression of a coding region selected from Table I; and harvesting the virus produced by the cells.

Embodiment 47

The method of embodiment 34, 35, 37, or 39 wherein the virus is a picornavirus.

Embodiment 48

The method of embodiment 47 wherein the picornavirus is a poliovirus

Embodiment 49

The method of embodiment 48 wherein the poliovirus is chosen from either Sabin 1, Sabin 2, or Sabin 3.

Embodiment 50

The method of embodiment 48 wherein the poliovirus is selected from Mahoney or Brunhilde.

Embodiment 51

The method of embodiment 48 wherein the poliovirus is MEF-1.

Embodiment 52

The method of embodiment 48 wherein the poliovirus is Saukett.

Embodiment 53

The method of embodiment 49 wherein cells of the cell line comprise two or three polioviruses.

Embodiment 54

The method of embodiment 47 wherein the picornavirus is enterovirus 71.

Embodiment 55

The method of embodiment 34, 35, 37, or 39 wherein the cell line is a mammalian cell line, an avian cell line, or an insect cell line.

Embodiment 56

The method of embodiment 55 wherein the mammalian cell line is selected from a human cell line, a non-human primate cell line, a canine cell line, or a hamster cell line Embodiment 57

The method of embodiment 56 wherein the mammalian cell line is HEp-2 or Vero P.

Embodiment 58

The method of embodiment 55 wherein the avian cell line is a chicken cell line, or a duck cell line.

Embodiment 59

A method for making an engineered cell comprising: introducing into a cell a molecule for editing the genome of the cell; incubating the cell comprising the molecule under conditions suitable for editing of the genome to occur; obtaining an engineered cell comprising an edited genome, wherein the editing results in decreased expression of a coding region selected from Table I compared to a control cell line.

Embodiment 60

The method of embodiment 60 wherein the molecule for editing the genome of the cell is a zinc finger nuclease, a meganuclease, or a transcription activator-like effector.

Embodiment 61

A method of treating a subject having or at risk of having a viral infection comprising increasing, in cells of the subject, expression of a coding region selected from Table I.

Embodiment 62

A method of treating a subject having or at risk of having a viral infection comprising inhibiting, in cells of the subject, expression of a coding region selected from Table II.

Embodiment 63

A method for treating a subject having or at risk of having a viral infection comprising inhibiting expression, in cells of the subject, of an endogenous miRNA selected from miR-520e, miR-1256, miR-520d-3p, miR-513a-5p, miR-519c-3p, miR-1270-2, miR-3187, miR-5763p, miR-22, miR-520c-3p, and miR-9.

Embodiment 64

A method for treating a subject having or at risk of having a viral infection comprising increasing, in cells of the subject, expression of an miRNA selected from Table IV.

The present invention is illustrated by the following examples. It is to be understood that the particular examples, materials, amounts, and procedures are to be interpreted broadly in accordance with the scope and spirit of the invention as set forth herein.

Example 1

General Methods

Both HEp-2C (also referred to as "HEp-2" cells in this document) and Vero P cells were maintained in Dulbecco's modified Eagle's medium (DMEM, Thermo Fisher Scientific, Cat. # Sh30243.01) supplemented with 10% calf serum (HyClone, Cat. # Sh30396.03) and containing 1% penicillin-streptomycin (Cellgro, Cat. #30-004-CI) during propagation. The human epidermoid cell line, HEp-2C, used for primary screening was derived from a single batch at passage 166. Vero cells (African Green Monkey kidney cells) were received from the Centers For Disease Control and Prevention, Atlanta (p.12).

For HTS siRNA transfections in the primary screen, On-TARGETplus (OTP)-siRNAs (Thermo Fisher Scientific, Dharmacon Products) were reverse transfected into HEp-2C cells at a final siRNA concentration of 50 nM in 0.3% DharmaFECT4 (DF4, Thermo Fisher Scientific, Cat. No. T-2004-01s) with 7,500 HEp-2C cells/per well in a 96-well plate. To achieve this, DF4 was first diluted in serum-free medium (OPTI-MEM) for 5 minutes. This material was then added to 96-well culture plates containing 5 µl of a 1 µM siRNA solution. The DF4-siRNA mixture was then incubated for 20 minutes (room temperature) prior to the addition of cells in Dulbecco's Modified Eagle's Medium supplemented with 10% calf serum. Transfected cells were then cultured for 48 hrs at 37° C., 5% $CO_2$. Subsequently, the media was removed and cells were infected at an MOI of 0.05 using a Sabin 2 Poliovirus Vaccine Strain that was diluted in DMEM containing 2% calf serum and 1% penicillin-streptomycin. For the primary screen, plates containing the virus-infected HEp-2C cells were removed from the culture incubator 24 hrs after virus infection and stored at −80° C. Each plate also contained multiple controls including: 1) siTox (Thermo Fisher Scientific, Cat. # D-001500-01-05), 2) siNon-targeting control (Thermo Fisher Scientific, Cat. No. D-001810-10-50), 3) poliovirus-specific siRNAs as a positive control targeting VP1 &3D (Thermo Fisher Scientific), and 4) a mock control.

For validation experiments a similar protocol that utilized Vero P cells was followed. Briefly, OTP-siRNAs were reverse transfected into Vero P cells at a final siRNA concentration of 50 nM in 0.3% DF4, with 7,500 cells/well. As described above, DF4 was diluted in serum-free OPTI-MEM for 5 minutes prior to adding the transfection reagent to 96-well culture plates containing 5 ul of a 1 μM siRNA solution. The DF4-siRNA cocktail was then incubated for 20 minutes at room temperature prior to addition of Vero P cells in DMEM supplemented with 10% calf serum. Transfected cells were then cultured for 48 hrs at 37° C., 5% $CO_2$. The media was then removed and cells were infected at an MOI of 0.05 using the Sabin 2 Poliovirus Vaccine Strain diluted in DMEM containing 2% calf serum and 1% penicillin-streptomycin. The plates containing the virus-infected Vero P cells were removed from culture 48 hrs later and stored at −80° C. before ELISA experiment.

Silencing Reagents siRNAs

The ON-TARGETplus siRNA (OTP-siRNA) library (Thermo Fisher Scientific) was used for the primary RNAi screen. OTP silencing reagents are provided as a pool of siRNA targeting each gene. Each pool contains 4 individual siRNAs targeting different regions of the open reading frame (ORF).

For validation experiments, each of the individual siRNA comprising the OTP pool was tested individually to determine if two or more siRNA generated the observed phenotype. Similarly, individual, unmodified siRNA derived from the siGENOME collection (Thermo Fisher Scientific, Dharmacon Products) and targeting gene hits identified in the primary screen were also tested for the ability to induce the desired phenotype. Non-targeting controls used in this work were purchased from Thermo Fisher Scientific (siGenome NTC, Thermo Fisher Scientific, Cat. No. D-001210-10-01-05).

miRNA Mimics and Inhibitors

The miRIDIAN library (Thermo Fisher Scientific, Dharmacon Products) of miRNA mimics was employed to identify host-encoded miRNAs that modulated poliovirus infection. Mimics were introduced into HEp-2C cells by transfection with DharmaFECT4.

Cell Viability Assay and Cell Proliferation Assay

To examine whether the transfection of siRNA negatively affected screen results by inducing cellular toxicity, we incorporated the ToxiLight™ bioassay (LONZA Inc.) in both the primary screen and hit validation studies. ToxiLight™ is a non-destructive bioluminescent cytotoxicity assay designed to measure toxicity in cultured mammalian cells and cell lines. The method, which quantitatively measures the release of adenylate kinase (AK) from damaged cells, was employed by assessing the culture supernatant 48 hours after siRNA transfection. To examine whether knock-down of the identified target genes affected cell growth, we employed the CellTiter 96® Assay (PROMEGA Inc., Kit cat. # G3580) to determine viable cell numbers. The CellTiter 96® Assay has been shown to provide greater signal sensitivity and stability compared to other MTT assays. In our studies, 48 or 72 hrs after siRNA transfection, the substrate for the CellTiter 96® Assay assay was added directly to the culture plates. Following a 4 hr incubation at 37° C., the culture absorbance was measured at OD495 nm.

The Poliovirus Type 2 ELISA

The poliovirus type 2 antigen-capture ELISA was designed to detect authentic poliovirus antigen ("D-antigen"), using a "sandwich" assay format. Briefly, the poliovirus type 2-specific mouse monoclonal antibody (HYB294-06, Thermo Scientific/Pierce) was diluted 1:500 in 0.05 M carbonate-bicarbonate buffer, pH 9.6. 50 μl of the diluted antibody was then dispensed into Immunlon 2HB high-binding 96-well plates (NUNC, Inc.) which were then incubated for 16 hours (overnight) at 4° C. in a moist chamber. The antibody-coated plates were then washed four times with phosphate-buffered saline, pH 7.2, supplemented with 0.05% Tween-20 (PBS-T), followed by incubation with 100 μl of a blocking buffer (PBS containing 0.5% gelatin and 0.25% Tween-20, 60 min at 37° C.). The plates were then subjected to four (4) washes with PBS-T. In the siRNA Hep-2C screen where the samples were treated with siRNA and subsequently infected with poliovirus for 24 hrs, 50 μl of the supernatant was added to each well of the antibody-coated plates and incubated for 60 min at 37° C. in a moist chamber. The plates were then washed four times with PBS-T, followed by incubation with 50 μl of HRP-conjugated monoclonal antibody (HYB 293-06, 1:1000 dilution) for 60 minutes at 37° C. in a moist chamber. Following four additional washes with PBS-T, 50 µl of the substrate (Sure-Blue Reserve, Kirkegaard and Perry Laboratories, 50-85-31) was added to each well. The plates were then incubated at room temperature for 15 minutes and the reaction was stopped by addition of 50 µl of TMB BlueSTOP Solution (Kirkegaard and Perry Laboratories, 50-85-31). Plates were then evaluated on a spectrophotometer at wavelength of 620 nm.

For the Sabin 1 and Sabin 3 testing, Vero cells transfected with siRNAs targeting various genes were infected with the Sabin 1 or Sabin 3 viruses. Subsequently, the supernatant was tested by ELISA, as above, using monoclonal antibodies specific for poliovirus type 1 (NBP1-05101, Novus Biologicals) or poliovirus type 3 (HYB 300-06, Thermo Scientific/Pierce), as appropriate, substituted for the type 2-specific antibody in the capture and conjugate steps.

Data Analysis Methods Used in the HTS Screening

Quality control was assessed using Z'-factor where a Z'-factor score between 0.5 and 1.0 is indicative of a highly robust assay whereas scores between 0 and 0.5 are deemed acceptable (see Zhang et al. (1999) *J. Biomol Screen* 4(2): 67-73). Data was normalized across the entire plate allowing us to set the mean (µ) of the data to zero and the standard deviation (SD) to 1. Positive hits from the primary screen are scored by Z-score.

Plaque and Cell Culture Infective Dose ($CCID_{50}$) Assays $CCID_{50}$ and plaque assays were performed to assess the effects of gene knockdown on live virus production. To achieve this, Vero cells (African Green Monkey Kidney cells) were transfected with siRNA targeting genes identified in the primary screen. Cultures were then infected with Sabin 2 poliovirus and the resultant supernatant was assessed in either the $CCID_{50}$ or plaque assays using HEp-2C cells. To study the effect of gene silencing events on the amounts of infectious virus particles, the 50% cell culture infective dose ($CCID_{50}$) was determined for Sabin-2 viruses produced in siRNA transfected Vero cells by means of end point dilution. In a 96-well format, ten-fold serial dilutions of the virus-containing supernatant (dilutions: $10^{-2}$ to $10^{-9}$, with 11 replicates per dilution) were incubated with HEp-2C cells (7,500/well). On each plate, eight virus-negative cell controls were included. Plates were incubated at 37° C., 5% $CO_2$ for 5 days, after which remaining live cells were visualized by removing the cell culture medium and staining with crystal violet reagent. The $CCID_{50}$ was calculated using the Spearman-Karber method (Kärber G (1931) Beitrag zur kollektiven behandlung pharmakologischer reihenversuche. Archiv für Experimentalische Pathologie and Pharmakologie 162:480-483). Plaque assays were performed to determine the effect of hit gene silencing on the amount of infectious virus particles produced. In a 6-well format, monolayers of HEp-2C cells (confluency of 80 to 90%) were incubated at 37° C. for 1 hour with ten-fold serial dilutions of Sabin 2 virus-containing supernatants from siRNA transfected Vero cells ($10^{-4}$ to $10^{-9}$ dilutions). Virus-containing supernatants from cells transfected with a non-targeting siRNA and from cells transfected with a poliovirus targeting siRNA were included as negative and positive controls, respectively. Cells were subsequently covered by agarose and incubated for 48 hours at 37° C., in 5% $CO_2$. Plaques were visualized by removing the agarose and staining of viable cells with formalin containing crystal violet reagent. Plaques were counted and used to calculate the amount of infectious virus particles in terms of plaque forming units per 1 ml of the selected supernatants. Plaque numbers and sizes were analyzed in comparison to those from the non-targeting control and the control with the Sabin 2-targeting siRNA.

Antigen Equivalency

To study the effect of silencing expression of hit genes on the antigenicity of viruses produced, a microneutralization assay was performed with Sabin 2 viruses from Vero cells transfected with siRNAs against selected genes and a pool of human sera collected from individuals previously exposed to poliovirus vaccine. In a 96-well format, 100 $CCID_{50}$ of Sabin 2 viruses from selected cell supernatants were combined with two-fold serial dilutions of the anti-polio serum, starting with a 1:8 dilution up to 1:1024. Sabin 2 viruses from cells not transfected with any siRNA were included as a control. Viruses and serum were incubated for 3 hours after which HEp-2C cells were added. After 5 days of incubation at 37° C., in 5% $CO_2$, cells were stained with crystal violet and endpoint serum neutralization titers calculated by the Spearman-Kärber formula (Kärber G (1931) Beitrag zur kollektiven behandlung pharmakologischer reihenversuche. Archiv für Experimentalische Pathologie and Pharmakologie 162:480-483).

Example 2

Primary Screen Results

Using the techniques described above, >18,200 genes from the human genome, including genes from the protease, ion channel, ubiqutin, kinase, phosphatase, GPCR, and drug target collections were screened (in triplicate) to identify gene knockdown events that enhanced poliovirus replication. FIG. 1 shows a plot of the Z-scores obtained from the primary screen. As indicated, only a small fraction of the total gene knockdown events gave scores equal to or greater than 3.0 standard deviation (SD) from the mean (124 genes, 0.68% of the total number of genes screened). The genes contained in this collection were distributed across multiple functional families (kinases, proteases, phosphatases, etc.) and included a significant number of targets not previously identified as "antiviral". In addition, over 100 gene silencing events were identified that greatly reduced poliovirus replication. These genes represent a potentially valuable collection of therapeutic targets in future anti-viral drug discovery efforts.

Table I identifies 128 gene knockdown events. A total of 124 gene knockdown events gave ELISA scores that were three (3) or more standard deviations above the mean. Twenty-eight (28) of these genes gave SD values greater than 4.0, and a single gene gave an SD value of 5 or greater. Four of these genes gave SD values between 2 and 3. Table I also presents the KEGG gene accession numbers (NM_), and Z score values. Table II identifies the list of gene knockdown events that gave ELISA scores that were two (2) SD or more below the mean.

Example 3

Pool Deconvolution Validation Studies

The first step in validating the gene targets identified in the primary screen involved demonstrating that two or more individual siRNAs targeting the same gene (but having non-identical seed sequences, i.e., nucleotides 2-7 of the antisense strand) generated the same phenotype. To perform this study, the four siRNA making up the OTP pool used in the primary screen were tested individually. Separately, a collection of unrelated siRNA reagents targeting the same gene(s) and derived from the siGENOME siRNA collection (Dharmacon Products, Thermo Fisher Scientific) were also tested.

Results from the validation study are presented in Table III and show that for 54% (68 genes) of the primary screen hits that gave SD values of 3.0 or greater, two or more siRNA targeting a given gene induced the same phenotype as the original OTP pool. These findings strongly support the conclusion that knockdown of the target genes in this list enhance poliovirus antigen and virus production. It should be noted that while only a single siRNA induced the desired phenotype for the remaining genes, this result does not eliminate the possibility that the identified gene(s) play an anti-viral role during poliovirus infection.

TABLE III

List of 68 genes where two or more siRNA were shown to increase poliovirus replication. Accession number provided in previous tables.

| Gene name | # of siRNAs |
|---|---|
| NEDD9 | 7 |
| PKIG | 6 |
| ARHGEF2 | 5 |
| EP300 | 5 |
| MUC1 | 5 |
| RNF20 | 5 |
| SEC61A1 | 5 |
| CHD5 | 4 |
| ETS1 | 4 |
| IQGAP3 | 4 |
| MAOA | 4 |
| ZNF205 | 4 |
| BCL9L | 3 |
| BET1L | 3 |
| C1orf210 | 3 |
| CD300LB | 3 |
| CETN1 | 3 |
| CHCHD7 | 3 |
| CYP1A2 | 3 |
| IRS4 | 3 |
| LOC120824 | 3 |
| LY6G6C | 3 |
| OR10A7 | 3 |
| OR10H1 | 3 |
| PEAR1 | 3 |
| RASSF4 | 3 |
| SEC31B | 3 |
| SIN3B | 3 |
| SLC39A14 | 3 |
| SPATA13 | 3 |
| UGCG | 3 |
| VGLL2 | 3 |
| VILL | 3 |
| YBX1 | 3 |
| ZDHHC4 | 3 |
| SLC1A2 | 2 |
| BOLL | 2 |
| BTN2A1 | 2 |
| C17orf47 | 2 |
| CCL7 | 2 |
| CDR2 | 2 |
| CNTD2 | 2 |
| COLEC11 | 2 |
| DPM2 | 2 |
| DZIP1 | 2 |
| FAM83D | 2 |
| GALNACT-2 | 2 |
| GLRXL | 2 |
| HEPN1 | 2 |
| HR | 2 |
| KRTAP4-4 | 2 |
| MANSC1 | 2 |
| MCCD1 | 2 |

TABLE III-continued

List of 68 genes where two or more siRNA were shown to increase poliovirus replication. Accession number provided in previous tables.

| Gene name | # of siRNAs |
|---|---|
| MED31 | 2 |
| MELL1 | 2 |
| MTX3 | 2 |
| NECAB2 | 2 |
| PAGE2B | 2 |
| PATE2 | 2 |
| PRAMEF8 | 2 |
| SEC61G | 2 |
| SIGLEC5 | 2 |
| STAU | 2 |
| TBC1D29 | 2 |
| TMSB4Y | 2 |
| TUBB8 | 2 |
| VDR | 2 |
| ZNF135 | 2 |

Example 4

Effects of Gene Knockdown on Live Poliovirus Production in Vero Cells

As further validation of the hits identified in the primary screen, $CCID_{50}$ and plaque assays were performed. Example results from these studies are shown in FIGS. 2 and 3. $CCID_{50}$ findings (FIG. 2) showed that several of the hits identified in the primary screen greatly increase live poliovirus titer by four- to twenty seven-fold (4-27×). These findings not only support prior deconvolution studies but also show 1) the identified gene knockdown events increase live virus production, and 2) gene knockdown events increase live virus production in a non-human (Vero) cell line currently used in poliovirus vaccine manufacturing.

Plaque assays support the $CCID_{50}$ findings. As exemplified in FIG. 3A, knockdown of multiple genes including but not limited to SLC1A2, ETS1, EP300, and PKIG results in dramatic increases in viral production as measured by the number of viral plaques. FIG. 3B provides results for over a dozen genes. siRNA-mediated knockdown of six of the genes (BCL9, GLRXP3, LY6G6C, ETS1, GPR30, and PATE2) increased live virus titer between five- and ten-fold (5-10×). Silencing of five other genes including BTN2A1, SEC61A1, Collec11, Sin3B, and SLC1A2 increased live viral titers by ten- to twenty-fold (10-20×) in Vero cells. Remarkably, two gene knockdown events (PKIG and EP300) enhanced viral titers by greater than twenty-fold (>20×) in the plaque assay. As described previously, gene functions fall into multiple families/functions including histone acetylases (EP300), protein kinase inhibitors (PKIG), solute carriers (SLC1A2) and more. Overall, these findings, in conjunction with the reported deconvolution studies, strongly support the conclusion that single gene knockdown/knockout events can significantly increase poliovirus antigen and replication.

Example 5

Antigen Equivalency

To study the effect of silencing expression of hit genes on the antigenicity of viruses produced, a microneutralization assay was performed with Sabin 2 viruses from Vero cells transfected with siRNAs against selected genes and a pool of human sera collected from individuals previously exposed to poliovirus vaccine. In a 96-well format, 100 $CCID_{50}$ of Sabin 2 viruses from selected cell supernatants were combined with two-fold serial dilutions of the anti-polio serum, starting with a 1:8 dilution up to 1:1024. Sabin 2 viruses from cells not transfected with any siRNA were included as a control. Viruses and serum were incubated for 3 hours after which HEp-2C cells were added. After 5 days of incubation at 37° C., in 5% $CO_2$, cells were stained with crystal violet and endpoint serum neutralization titers calculated by the Kärber formula (Kärber G (1931) Beitrag zur kollektiven behandlung pharmakologischer reihenversuche. Archiv für Experimentalische Pathologie and Pharmakologie 162:480-483).

As shown in FIG. 4, of the 18 gene targets tested, all demonstrate equivalent or better cross-reactivity. These findings support the notion that vaccine cell lines modified with siRNA to enhance poliovirus production generate viral particles that are recognized by antibodies present in serum taken from individuals previously exposed to the poliovirus (i.e., antigenic equivalency).

Example 6

Sabin 1 and Sabin 3 Studies

The virulent parental strains of the three poliovirus vaccine (Sabin) strains are LSc/2ab (serotype 1), P712 (serotype 2), and Leon (serotype 3). Sabin 1 has 57 nucleotide substitutions that distinguish it from the parental LSc/2ab virus. Similarly, Sabin 2 and Sabin 3 have two and 10 nucleotide substitutions (respectively) that distinguish them from the P712 and Leon strains, respectively.

Figure 5A:
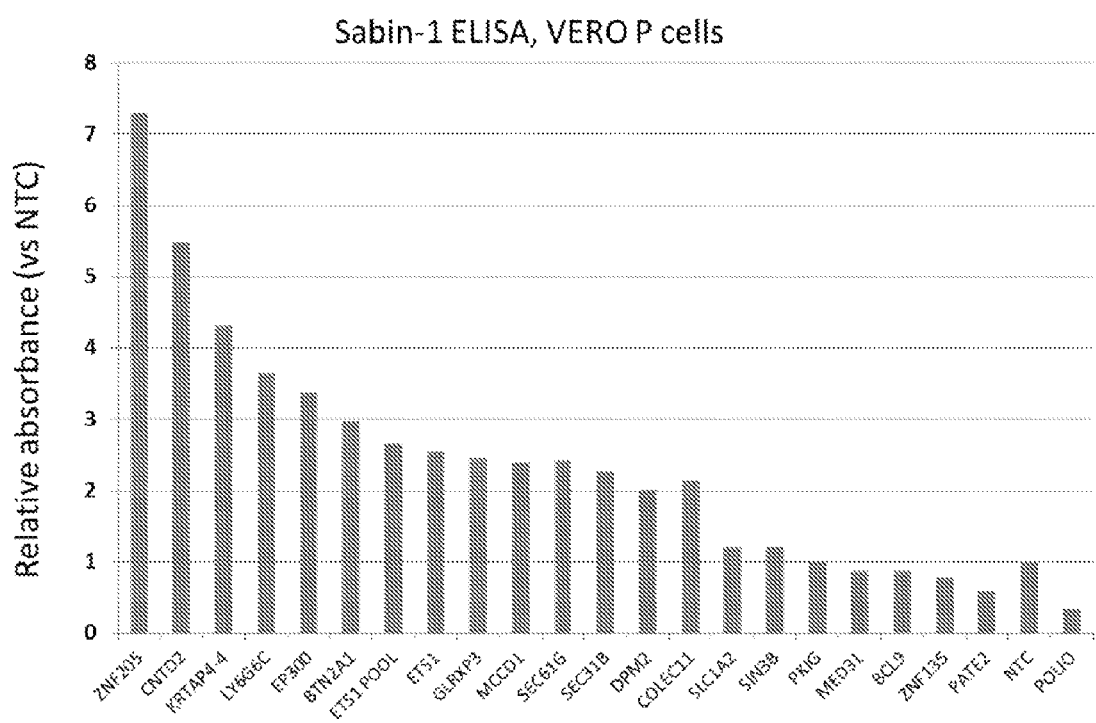
Figure 5B:
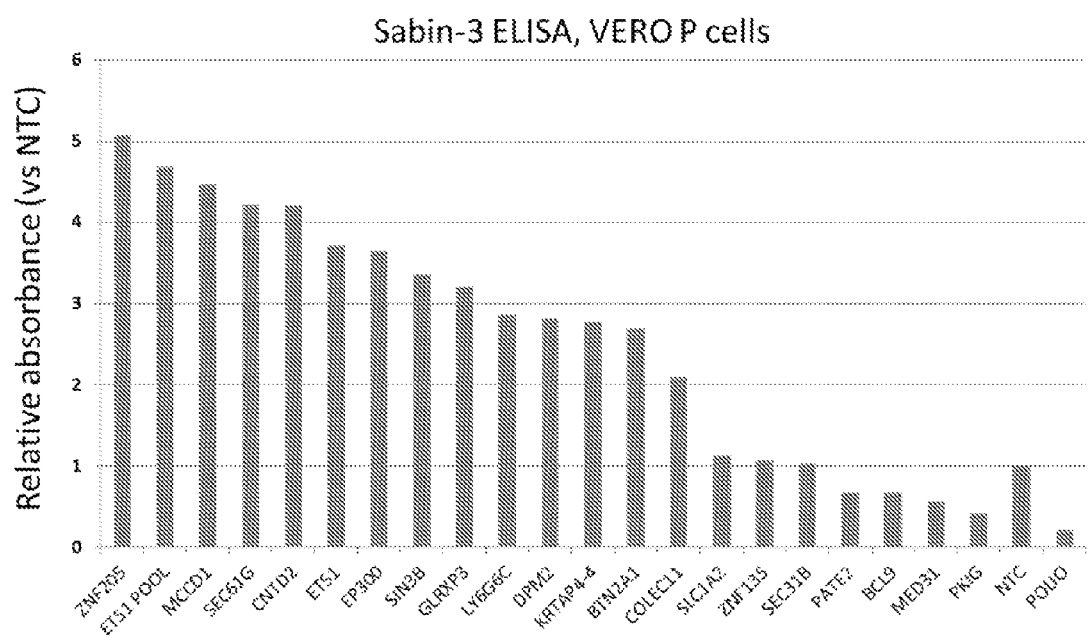

As current vaccines incorporate all three attenuated serotypes (Sabin 1, 2, and 3), we tested how target genes identified in our Sabin 2 primary screen affected Sabin 1 and 3. To achieve this, siRNA targeting twenty-one of the genes 1) identified in the Sabin 2 screen, and 2) validated were introduced into Vero cells. Cells were then infected with either Sabin-1 or Sabin 3 virus and supernatants were subsequently assessed using ELISA. Results of these studies showed that for both Sabin 1 and Sabin 3, fourteen of the twenty-one genes tested increased ELISA absorbance scores by two-fold or more (FIG. 5A, 5B). The highest absorbance increases for both viruses (for Sabin 1 and Sabin 3, 7× and 5×, respectively) resulted from knockdown of ZNF205. Overall, because a significant overlap existed between the list of gene targets that increased viral production for all three serotypes, these findings show that hits identified in Sabin 2 viral screen can be extended to other picornaviruses.

Figure 5C:
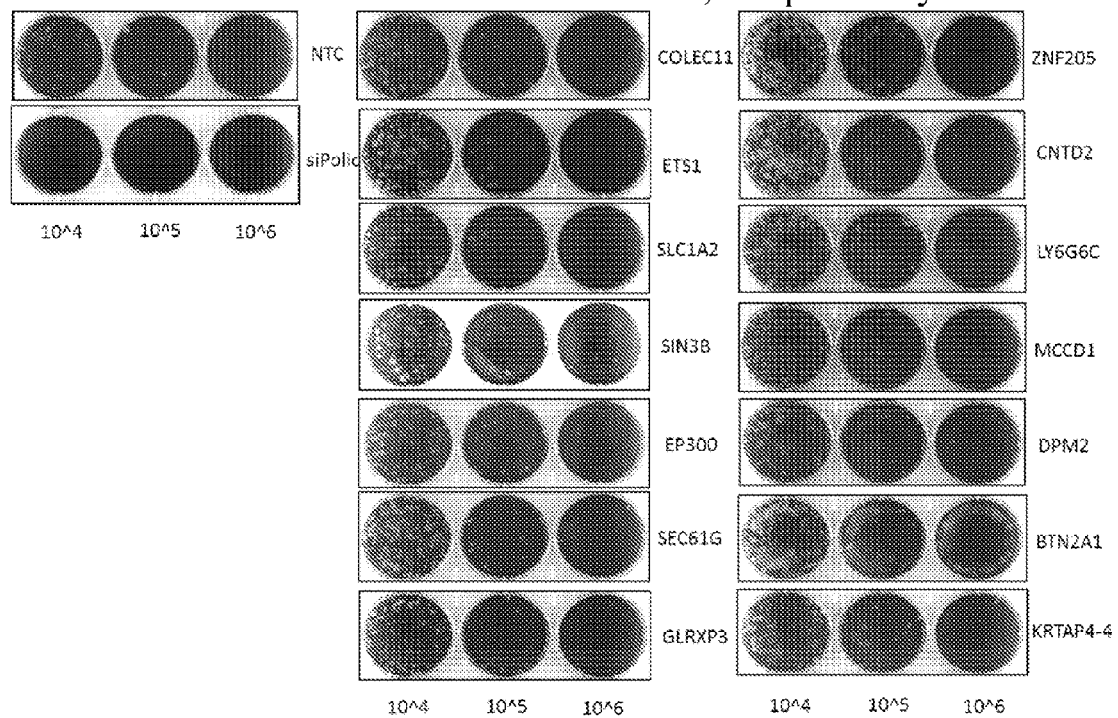
Figure 5D:
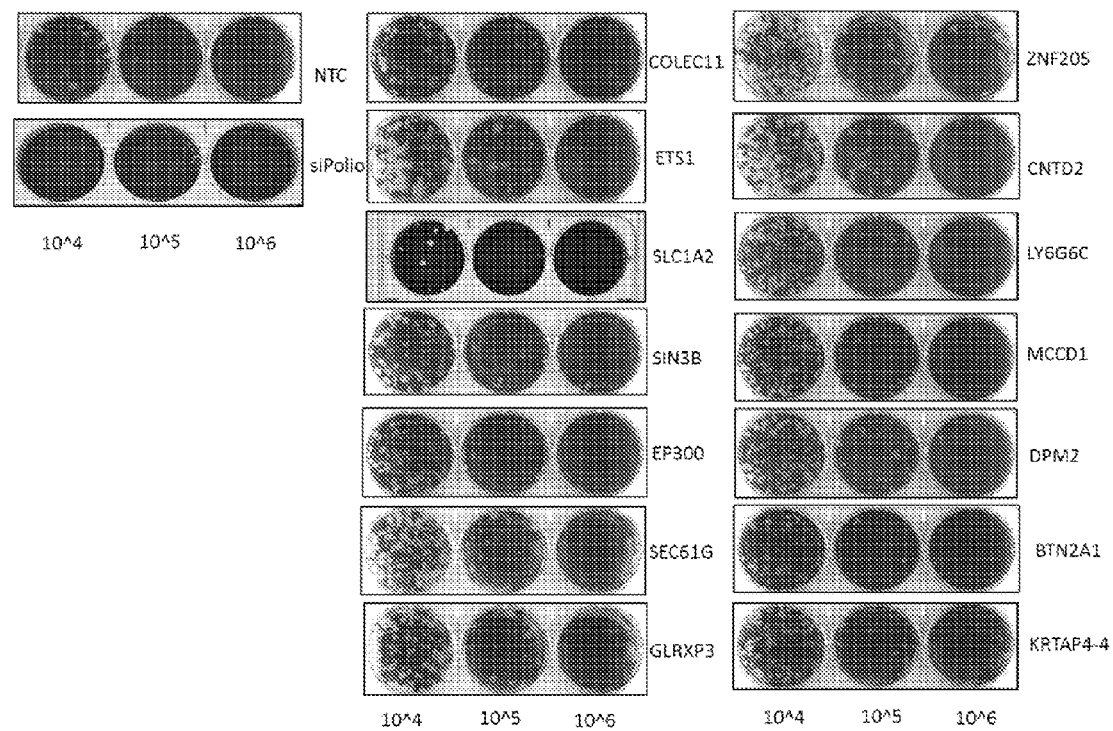

Using the techniques described previously, plaque assays were also performed using Sabin 1 and Sabin 3 viruses. The results support those found in the ELISA assay, and demonstrate that several of the hits identified in the Sabin 2 screen also elevate Sabin 1 and Sabin 3 production (FIGS. 5c and 5d, respectively).

Using the techniques described above, antigen equivalency studies were performed on Sabin 1 and Sabin 3 viruses produced in cells that had been modified with siRNA targeting genes identified in the primary Sabin 2 screen. As observed in the Sabin 2 antigen equivalency studies, gene knockdown had little or no effect on Sabin 1 and Sabin 3 antibody titers (data not shown), supporting the conclusion that virus produced in cells that had been modified with siRNA targeting the genes of interest are indistinguishable from those produced in control cells.

Example 7 miRNA Mimic Screening

To identify host-encoded miRNAs that enhance poliovirus production, HEp-2C cells were transfected with over 1,200 different miRNA mimics and subsequently infected with Sabin 2 virus. The resultant supernatants were then analyzed with the poliovirus-specific ELISA described in Example 1.

As was the case for the siRNA screen (Example 2), only a small fraction of the total miRNA population enhanced viral production (FIG. 6). To further assess the value of miRNA mimics in the production of live virus, $CCID_{50}$ validation studies were performed in Vero cells. From this collection, eleven miRNAs enhanced poliovirus production by two-fold or more (FIG. 7). Five genes including miR-520e, miR-1256, miR-520d-3p, miR-513a-5p, and miR-519c-3p, enhance poliovirus antigen and virus production by two- to four-fold. Six miRNAs (miR-1270-2, miR-3187, miR-5763p, miR-22, miR-520c-3p, and miR-9) were shown to increase live poliovirus production by four- to twelve-fold (4-12×). The nucleotide sequence of these miRNAs is available from the microRNA database, the miR Base, which is available at mirbase.org. These miRNAs can be used individually or in combination with other miRNAs, miRNA inhibitors, siRNAs targeting protein encoding genes, and/or cloned DNA or ORF expression constructs to increase poliovirus protein and/or virus production.

In addition to identifying multiple miRNAs that enhanced poliovirus antigen and virus production, the primary miRNA screen identified multiple miRNAs that decreased poliovirus production (see Table IV). These miRNAs can be used individually or in combination with other miRNAs, miRNA inhibitors, siRNAs targeting protein encoding genes, and/or cloned DNA or ORF expression constructs to 1) decrease poliovirus replication in a therapeutic setting, or 2) identify therapeutic targets to combat poliovirus infection.

TABLE IV

List of miRNAs that decrease poliovirus antigen and virus replication.

| miR mimics | Normalized Z |
| --- | --- |
| hsa-miR-138 | −2.4403 |
| hsa-miR-134 | −2.3096 |
| hsa-miR-509-3p | −2.1850 |
| hsa-miR-1250 | −2.1730 |
| hsa-miR-29b | −2.0564 |
| hsa-mir-3132 | −2.0313 |
| hsa-miR-7-2* | −2.0278 |
| hsa-miR-769-3p | −1.9770 |
| hsa-miR-16 | −1.9572 |
| hsa-miR-342-5p | −1.8980 |
| hsa-miR-323-5p | −1.8961 |
| hsa-mir-3140 | −1.8811 |
| hsa-miR-1909 | −1.8725 |
| hsa-miR-522 | −1.8432 |
| hsa-miR-330-5p | −1.8413 |
| hsa-miR-29c | −1.8369 |
| hsa-miR-1275 | −1.8306 |
| hsa-mir-3118-1 | −1.8229 |
| hsa-miR-29a | −1.8126 |
| hsa-mir-3661 | −1.7807 |
| hsa-miR-1255b | −1.7509 |
| hsa-miR-424 | −1.7503 |
| hsa-miR-1182 | −1.7367 |

TABLE IV-continued

List of miRNAs that decrease poliovirus antigen and virus replication.

| miR mimics | Normalized Z |
|---|---|
| hsa-miR-421 | −1.7236 |
| hsa-miR-26b | −1.7231 |
| hsa-miR-129-3p | −1.7159 |
| hsa-mir-4265 | −1.6974 |
| hsa-miR-663 | −1.6806 |
| hsa-miR-544 | −1.6514 |
| hsa-miR-450b-3p | −1.6297 |
| hsa-miR-432 | −1.6267 |
| hsa-miR-523 | −1.6170 |
| hsa-miR-555 | −1.5986 |
| hsa-miR-1908 | −1.5895 |
| hsa-miR-320d | −1.5835 |
| hsa-miR-1181 | −1.5697 |
| hsa-miR-801 | −1.5610 |
| hsa-miR-924 | −1.5341 |
| hsa-miR-218-2* | −1.5341 |
| hsa-let-7d | −1.5057 |

Example 8

Broader Testing of Validated Targets in Vero Cells

The top 29 gene silencing events that increased poliovirus titers in HEp-2C cells, were further validated in Vero cells with seven different polio strains including three attenuated vaccine strains (Sabin 1, Sabin2, and Sabin 3), Mahoney (wild type 1), Brunhilde (wild type 1), MEF (wild type 2), and Saukett (wild type 3). To achieve this, individual siRNAs targeting the gene of choice were reverse transfected into Vero cells (6,000 cells/well, 96 well format, in Dulbecco's Modified Eagle's Medium (DMEM, Hyclone) supplemented with 10% fetal calf serum (FCS, Hyclone) at a final concentration of 50 nM. Gene targets and siRNA sequences are provided in Table V. Transfection was performed using DharmaFECT 4 Transfection reagent (0.35%). All transfections were performed in triplicate. Quantitative PCR experiments were performed to estimate the level of gene silencing for each of the siRNA used in these experiments. Control studies for these experiments included 1) cells transfected with a poliovirus-specific siRNA targeting the poliovirus capsid encoding region, and 2) a non-targeting control siRNA (NTC). Cells were then incubated at 37° C., 5% $CO_2$ and 16 to 24 hours after siRNA transfection the cell culture medium was refreshed. Forty-eight hours after transfection, cells were infected with 60 $CCID_{50}$ of a Sabin-1 virus stock ($10^{8.6}$ $CCID_{50}$/ml), 30 $CCID_{50}$ of Sabin-2 ($10^{7.3}$ $CCID_{50}$/ml), 9.5 $CCID_{50}$ of Sabin-3 ($10^{6.8}$ $CCID_{50}$/ml), 8.4 $CCID_{50}$ of wild type 1 Mahoney virus ($10^{7.75}$ $CCID_{50}$/ml), 1 $CCID_{50}$ of wild type 1 Brunhilde virus ($10^{7.84}$ $CCID_{50}$/ml), 6.4 of wild type 2 MEF virus ($10^{7.63}$ $CCID_{50}$/ml), or 3.8 $CCID_{50}$ of wild type 3 Saukett virus ($10^{7.4}$ $CCID_{50}$/ml) in 150 µl DMEM supplemented with 2% FCS. Uninfected cells were included as a negative control. The cells were then incubated at 37° C., 5% $CO_2$ for 21 to 36 hours, depending on the type of virus, and subsequently frozen at −80° C. The supernatant was used to determine the virus titer by means of end point dilution. Briefly, in a 96-well format, 10-fold serial dilutions of the virus supernatant (starting with a $10^{-2}$ dilution up to $10^{-9}$) were incubated with HEp-2C cells (7,500/well, 11 replicates per virus dilution) at 37° C., 5% $CO_2$ for 5 days. The cells were stained with crystal violet and $CCID_{50}$ was calculated by scoring the cytopathic effect (CPE) in all wells using the Spearman-Kärber formula. In line with the generally accepted 0.5 $log_{10}$ variation observed among $CCID_{50}$ values in replicate experiments, the cut-off value for identifying hits was set at a 3.16 fold increase in virus titer compared to the NTC.

Table V

List of genes, accession numbers, and siRNA sequences that were used to generate data in FIG. 8

| Candidate gene | Accession No | Sequence (5' --> 3') |
|---|---|---|
| BCL9L | NM_182557 | AACCAGAUCUCGCCUAGCA |
| BTN2A1 | NM_007049 | GGGAGAGCGUGCCUGACAA |
| COLEC11 | NM_024027 | UGUCCAAGCUAUACAAUAA |
| DPM2 | NM_003863 | UGCCAUUCAUCGACAGUCA |
| CNTD2 | NM_024877 | AAACUGAGGUCCGGAACUU |
| MCCD1 | NM_001011700 | AAGAGUUGUUGGAGCAGCA |
| LY6G6C | NM_025261 | GGACAGCAAUGCCUGACAA |
| MED31 | NM_016060 | GUUUAGCCAACCCAAAUUA |
| PATE2 | NM_212555 | GGGUUAUGCUAUGGUGUCA |
| ZNF205 | NM_001042428 | GCGCACAACCGCACACACA |
| GLRXP3 | NM_001123388 | GAUUGGAGCUCUGCAGUAA |
| SEC61G | NM_014302 | UGAAAUUGAUCCAUAUUCC |
| KRTAP4-4 | NM_032524 | GCUGAGUUAUGGGAAGCUA |
| ZNF135 | NM_003436 | CGGAACAGCUCGGCACUUA |
| SEC31B | NM_015490 | CCUACAGGGUCACUCAGUA |
| SIN3B | NM_015260 | GCCAAGCGGUCUCUGUUCA |
| ACVR2B | NM_001106 | ACGAGAACCUGCUACAGUU |
| GCGR | NM_000160 | CCACGGAGCUGGUGUGCAA |
| OPN3 | NM_001030011 | AAAAGAAACUGGCCAAAAU |
| TAF1 | NM_004606 | CCAAGCAACUUCUACGUAA |
| CELSR3 | NM_001407 | GCCGAAAGCUAGACAAUAA |
| DTYMK | NM_012145 | GGGAACAAGUGCCGUUAAU |
| GPER | NM_001031682 | GGGUGAAGCGCCUCAGUUA |
| PAK1 | NM_002576 | UCAAAUAACGGCCUAGACA |
| TAF1L | NM_153809 | CCAAGCAACUUCUACGUAA |
| SLC1A2 | NM_004171 | GAUGAGUGCUAGAGAUGAA |
| ETS1 | NM_005238 | CAGAAUGACUACUUUGCUA |
| PKIg | NM_007066 | AGACAAGGAAGCUGGCAAC |
| EP300 | NM_001429 | GGACUACCCUAUCAAGUAA |

Figure 8A:
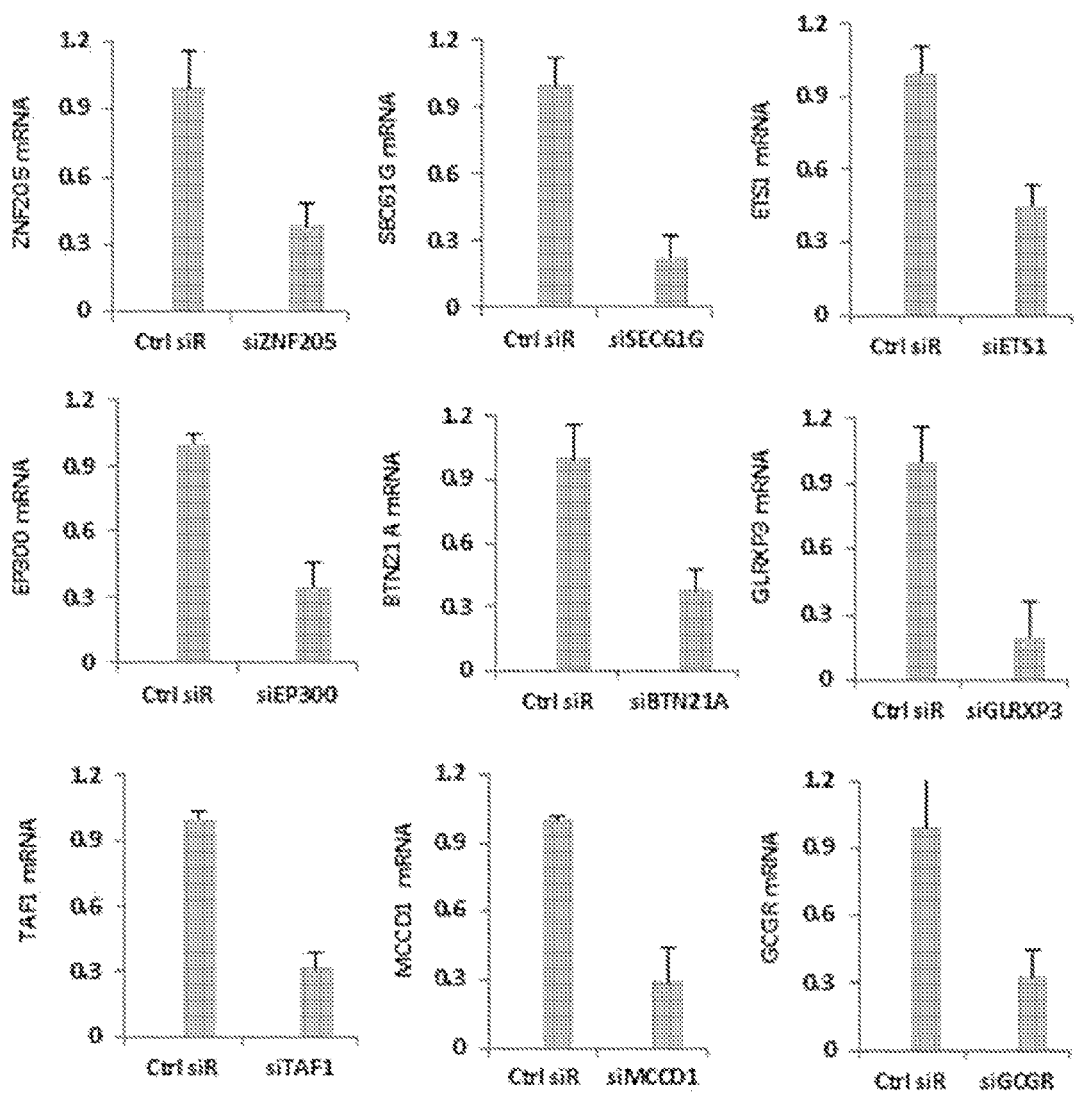
Figure 8B:
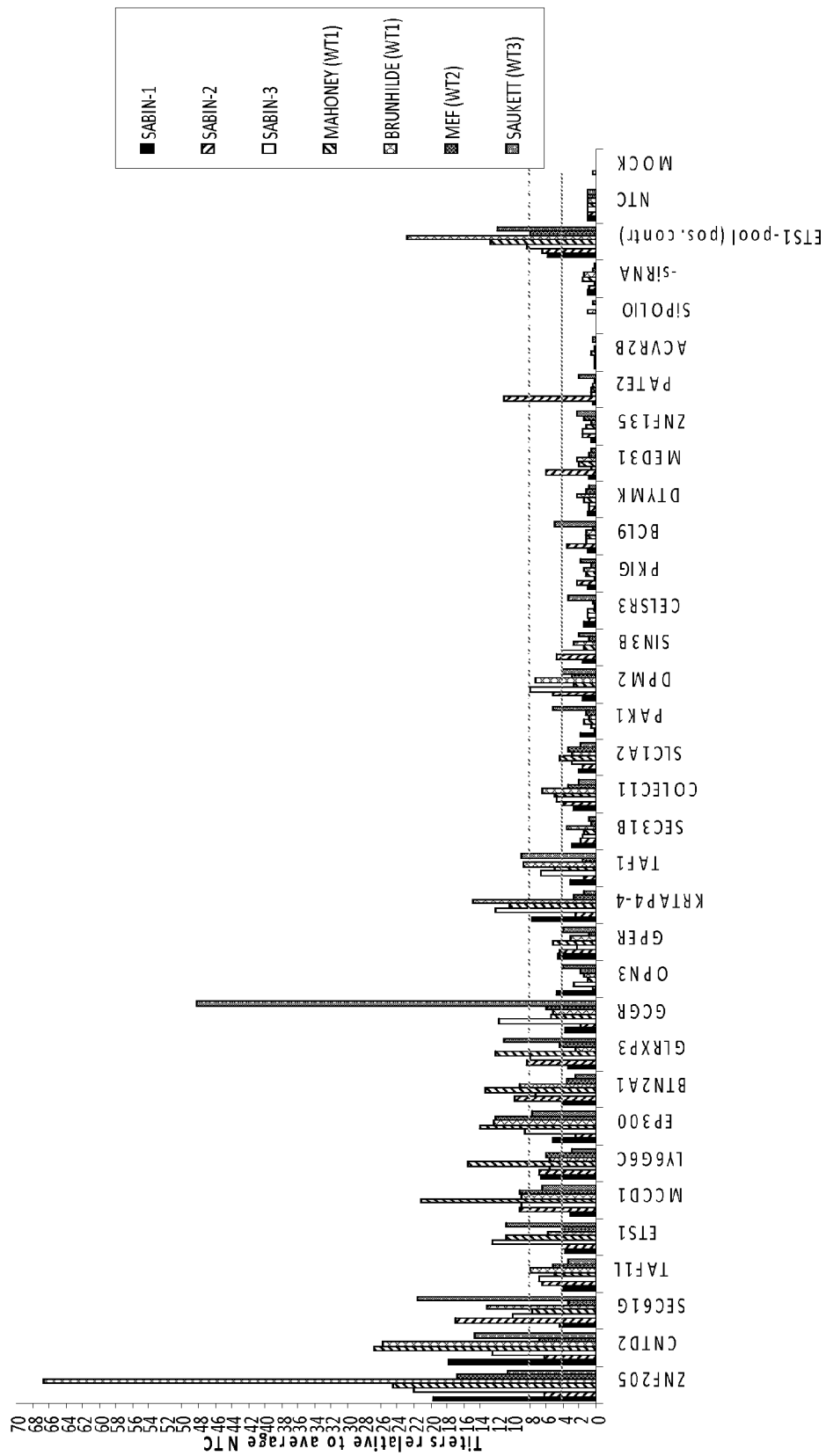

Results for these experiments are found in FIG. 8. FIG. 8a provides exemplary results from the quantitative PCR studies. Findings show that transfection of the siRNA typically induces ~70% or greater knockdown of target gene expression. FIG. 8b shows that when silenced, several of the top hits (e.g. ZNF205, CNTD2 (also referred to as FLJ13265), SEC61G, ETS1, MCCD1 (also referred to as LOC401250), LY6G6C, EP300, BTN2A1, GLRXP3 (also known as GLRXL), GCGR, KRTAP4-4, TAF1) significantly increase the titer of one or more of the polio strains.

Example 9

Identifying the Effects of Multigene Knockdown on Poliovirus Titers

Multiple genes from Example 8 were selected for subsequent studies to determine whether simultaneous knockdown of two separate genes further enhanced viral titers. To achieve this, pairs of siRNAs (targeting two separate genes) were reverse transfected into Vero cells (7,250 cells/well) at a final concentration of 50 nM (25 nM of each individual siRNA) using DharmaFECT 4 reagent (0.35%). Cells transfected with each combination of siRNA were then tested (in triplicate) with each of the seven viruses (Sabin 1 (vaccine), Sabin2 (vaccine), Sabin 3 (vaccine), Mahoney (wild type 1), Brunhilde (wild type 1), MEF (wild type 2), and Saukett (wild type 3)). As an internal experimental control, the individual siRNAs targeting each gene were also reverse transfected (in triplicate, 25 nM) on each plate to facilitate accurate assessment of the effects of dual gene knockdown.

Figure 9A:
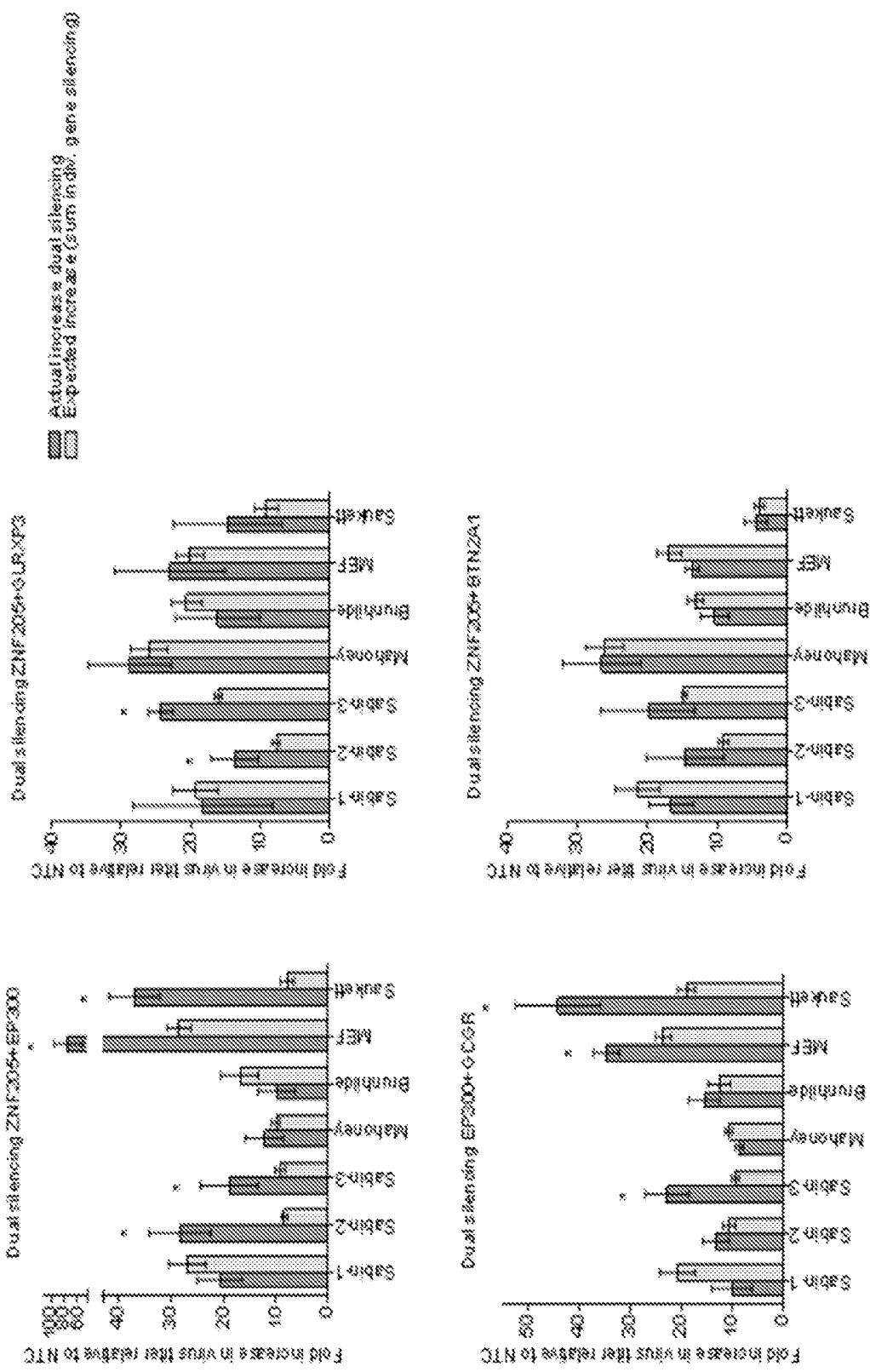
Figure 9B:
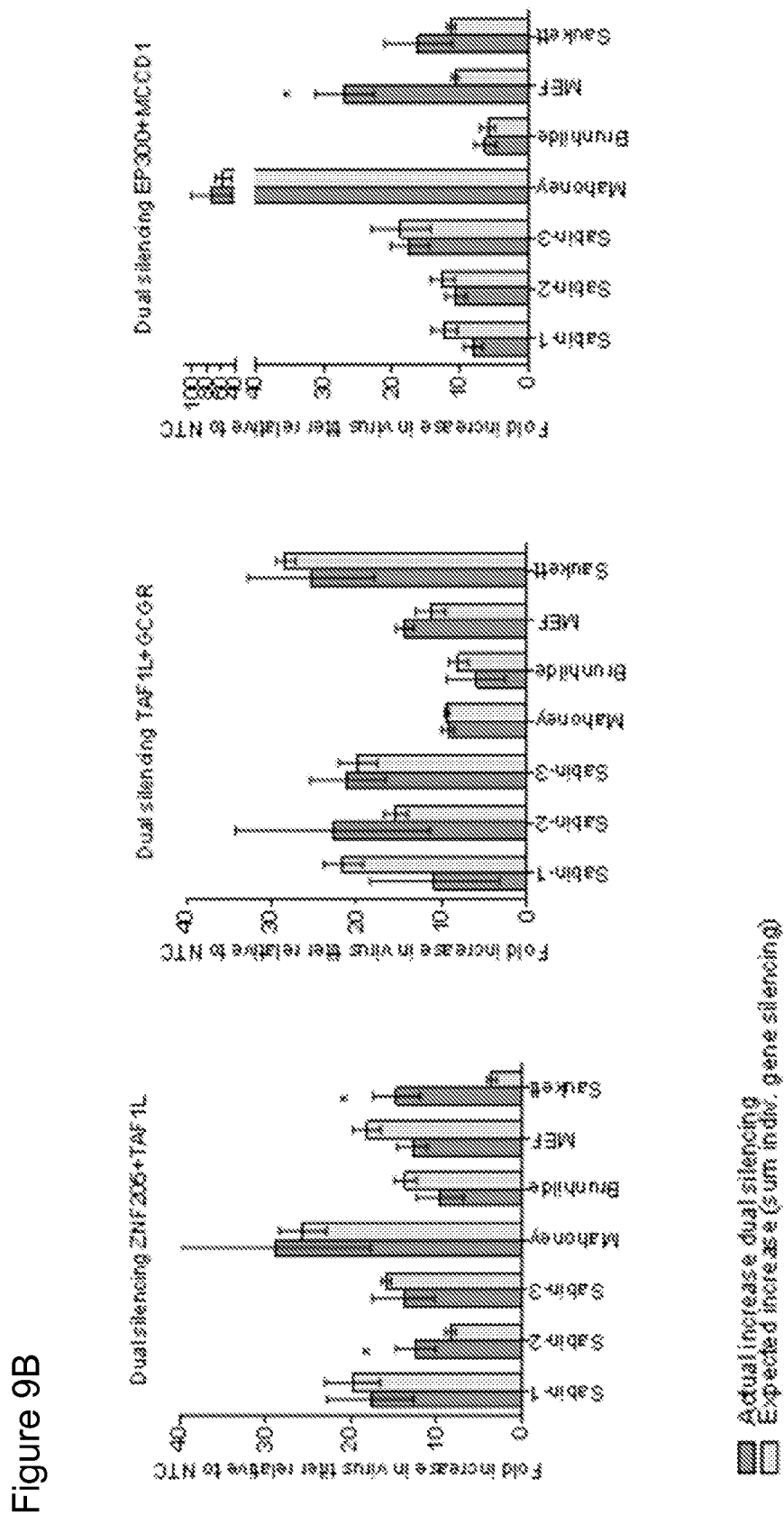

The results of these studies are reported in FIG. 9 and Table VI. FIGS. 9A and 9B shows exemplary data from our dual gene knockdown experiments and identifies multiple combinations that significantly enhance the production of one or more poliovirus strains in additive or synergistic (see "*") fashion. Table VI identifies 49 gene combinations that when simultaneously silenced, induced 1) synergistic effects (i.e., increases in viral titer that are greater than those predicted if both individual gene knockdown results were combined/added), or 2) additive effects (increases in viral titer that are equivalent or near-equivalent to the increases one would expect if the effects of the individual genes were combined) for at least one of the seven viruses tested. For instance, based on individual knockdown experiments performed alongside the dual knockdown investigations, simultaneous silencing of ZNF205 and EP300 are expected to increase MEF titers by roughly 28-fold if the effects were additive. Instead, simultaneous knockdown of these two genes resulted in (on average) a 65-fold increase in MEF titers. Similarly, based on individual knockdown experiments, silencing of EP300+GCGR is expected to give an 18 fold increase in Saukett titers if an additive effect occurred. Instead, when these two genes were simultaneously silenced, we observed (on average) a 40-45-fold increase. These findings and others identify previously unknown gene combinations that (when silenced) further enhance poliovirus production. The inventors predict that silencing three or four genes from this list could enhance poliovirus production even further. For example, a combination of [ZNF205+EP300+GLRXP3], or [ZNF205+EP300+ETS] are predicted to further increase poliovirus titers.

TABLE VI 49 gene combinations that enhance poliovirus production in an additive or synergistic fashion.

| Number | Gene Combinations |
|---|---|
| 1 | ZNF205 + EP300 |
| 2 | EP300 + GCGR |
| 3 | EP300 + MCCD1 |
| 4 | ZNF205 + BTN2A1 |
| 5 | ZNF205 + GLRXP3 |
| 6 | ZNF205 + SEC61g |
| 7 | BTN2A1 + TAF1L |
| 8 | BTN2A1 + GLRXP3 |
| 9 | EP300 + BTN2A1 |
| 10 | EP300 + GLRXP3 |
| 11 | CNTD2 + EP300 |
| 12 | ZNF205 + CNTD2 |
| 13 | BTN2A1 + ETS1 |
| 14 | ZNF205 + ETS1 |
| 15 | ZNF205 + MCCD1 |
| 16 | ZNF205 + GCGR |
| 17 | CNTD2 + GCGR |
| 18 | CNTD2 + MCCD1 |
| 19 | SEC61G + ETS1 |
| 20 | CNTD2 + GLRXP3 |
| 21 | ZNF205 + TAF1L |
| 22 | ZNF205 + LY6G6C |
| 23 | LY6G6C + BTN2A1 |
| 24 | TAF1L + GCGR |
| 25 | GCGR + GLRXP3 |
| 26 | TAF1L + ETS1 |
| 27 | LY6G6C + TAF1L |
| 28 | SEC61G + GCGR |
| 29 | BTN2A1 + GCGR |
| 30 | CNTD2 + BTN2A1 |
| 31 | CNTD2 + TAF1L |
| 32 | SEC61G + MCCD1 |
| 33 | EP300 + ETS1 |
| 34 | EP300 + SEC61G |
| 35 | GCGR + ETS1 |
| 36 | ETS1 + GLRXP3 |
| 37 | CNTD2 + ETS1 |
| 38 | SEC61G + TAF1L |
| 39 | LY6G6C + EP300 |
| 40 | TAF1L + GLRXP3 |
| 41 | LY6G6C + ETS1 |
| 42 | EP300 + TAF1L |
| 43 | CNTD2 + SEC61g |
| 44 | ETS1 + MCCD1 |
| 45 | GLRXP3 + MCCD1 |
| 46 | SEC61G + BTN2A1 |
| 47 | LY6G6C + GLRXP3 |
| 48 | LY6G6C + GCGR |
| 49 | GCGR + MCCD1 |

Example 10

Poliovirus is a member of the Picornaviridae family. To test how hits identified in our poliovirus screen affected other viruses belonging to the Picornaviridae family, experiments were performed with Enterovirus 71 (EV71). To achieve this, siRNAs targeting one of several genes identified during the PV RNAi screen were reverse transfected into Vero Cells (7,200 cells/well, 96 well format) at a concentration of 50 nM. Following a 64-72 hour period to allow for gene silencing, cells were infected with 3981 $CCID_{50}$ (50% cell culture infectious dose) of EV71, sub-genotype C2 (stock $10^{6.45}$ $CCID_{50}$/ml) in 150 microliters DMEM supplemented with 2% fetal calf serum. Cells were then incubated at 37° C., 5% $CO_2$ for 66 hours and subsequently frozen (−80° C.) before cultures were examined to determine the level of cytopathic effects (CPE) in each of the cultures. Experiments were performed in triplicate and incorporated a non-targeting control siRNA (NTC), an siRNA targeting the EV71 genome (siEV71), and mock transfection controls (-siRNA).

Results of these studies demonstrate that hits identified during the poliovirus screen also enhance the production of EV71. As shown in FIG. 10A, several of the gene knockdown events, including but not limited to MCCD1, ZNF205, GCGR and others, greatly enhance cytopathic effects, supporting the conclusion that gene silencing has significantly increased EV71 virus production. Additional experiments at the 66 hours post-infection time points support these conclusions (data not shown). Plaque assays were also performed to quantitate the observed increases in EV71 titers. As shown in a $1\times10^5$ (i.e., 1 in $10^5$) dilution of viral supernatants from these experiments, knockdown of ZNF205, CNTD2 and MCCD1 significantly increase the number of EV71 viral particles (see FIG. 10B). The bar graph shown in FIG. 10C shows that while CNTD2 and MCCD1 knockdown increase viral titers by approximately ten fold (10×), knockdown of ZNF205 increased titers by roughly 60 fold. Based on the results with poliovirus, the inventors believe combinations of these gene knockdown events would further enhance EV71 titers.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. Supplementary materials referenced in publications (such as supplementary tables, supplementary figures, supplementary materials and methods, and/or supplementary experimental data) are likewise incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. An engineered cell line, wherein cells of the engineered cell line comprise decreased endogenous expression of at least one coding region selected from Table I compared to a control cell line, wherein the at least one coding region is selected from ZNF205, CNTD2, SEC61G, ETS1, TAF1L, MCCD1, LY6G6C, BTN2A1, GLRXL, GCGR, or EP300, and wherein the cells comprise an edited genome that results in decreased endogenous expression of the coding region, wherein the edited genome comprises a mutation of the genomic DNA of the engineered cell compared to a control cell line.

2. An engineered cell line, wherein cells of the engineered cell line comprise decreased endogenous expression of at least one coding region selected from Table I compared to a control cell line, wherein the at least one coding region is selected from ZNF205, CNTD2, SEC61G, ETS1, TAF1L, MCCD1, LY6G6C, BTN2A1, GLRXL, GCGR, or EP300, wherein the cells comprise a mutation in the coding region or in a regulatory region operably linked to the at least one coding region.

3. An engineered cell line, wherein cells of the engineered cell line comprise decreased endogenous expression of at least one coding region selected from Table I compared to a control cell line, wherein the at least one coding region is selected from ZNF205, CNTD2, SEC61G, ETS1, TAF1L, MCCD1, LY6G6C, BTN2A1, GLRXL, GCGR, or EP300, wherein the cells further comprise decreased expression of at least one additional coding region selected from Table I, increased expression of an miRNA selected from miR-520e, miR-1256, miR-520d-3p, miR-513a-5p, miR-519c-3p, miR-1270-2, miR-3187, miR-5763p, miR-22, miR-520c-3p, and miR-9 compared to a control cell line, decreased expression of an endogenous miRNA selected from Table IV, or a combination thereof.

4. An engineered cell, wherein cells of the engineered cell line comprise increased endogenous expression of at least one coding region selected from Table II compared to a control cell line, wherein the cells further comprise increased expression of at least one additional coding region selected from Table II, decreased expression of an endogenous miRNA selected from miR-520e, miR-1256, miR-520d-3p, miR-513a-5p, miR-519c-3p, miR-1270-2, miR-3187, miR-5763p, miR-22, miR-520c-3p, and miR-9 compared to a control cell line, decreased expression of an endogenous miRNA selected from Table IV, or a combination thereof.

5. An engineered cell line, wherein cells of the engineered cell line comprise decreased endogenous expression of at least one coding region selected from Table I compared to a control cell line, and wherein the at least one coding region is selected from ZNF205, CNTD2, SEC61G, ETS1, TAF1L, MCCD1, LY6G6C, BTN2A1, GLRXL, GCGR, or EP300, and wherein the cells comprise an edited genome that results in decreased endogenous expression of the coding region, and wherein the cells comprise a picornavirus, wherein the edited genome comprises a mutation of the genomic DNA of the engineered cell compared to a control cell line.

6. The engineered cell line of claim 5 wherein the picornavirus is an enterovirus 71 or a poliovirus, chosen from either Sabin 1, Sabin 2, Sabin 3, Mahoney, Brunhilde, MEF-1, or Saukett.

7. A lysate of the engineered cell line of claim 1.

8. A method for producing a virus comprising: providing the engineered cell line of claim 1 wherein cells of the cell line comprise a virus; incubating the engineered cell line under conditions suitable for the production of the virus by the cells; and harvesting the virus produced by the cells.

9. The method of claim 8 wherein the incubating comprises a medium comprising (i) an RNA polynucleotide that inhibits expression of a coding region selected from Table I or (ii) a small molecule that inhibits expression of a coding region selected from Table I.

10. The method of claim 8 wherein the virus is a picornavirus.

11. The method of claim 10 wherein the picornavirus is an enterovirus 71 or a poliovirus, chosen from either Sabin 1, Sabin 2, Sabin 3, Mahoney, Brunhilde, MEF-1, or Saukett.

12. An engineered cell line, wherein cells of the engineered cell line comprise increased endogenous expression of at least one coding region selected from Table II compared to a control cell line, wherein the cells comprise a picornavirus, and wherein the picornavirus is an enterovirus 71 or a poliovirus chosen from either Sabin 1, Sabin 2, Sabin 3, Mahoney, Brunhilde, MEF-1, or Saukett.

13. An engineered cell line, wherein cells of the engineered cell line comprise decreased endogenous expression of at least one coding region selected from Table I compared to a control cell line, wherein the at least one coding region is selected from ZNF205, CNTD2, SEC61G, ETS1, TAF1L, MCCD1, LY6G6C, BTN2A1, GLRXL, GCGR, or EP300, and wherein the cells comprise a picornavirus.

14. The engineered cell line of claim 13 wherein the cells comprise (i) a mutation in the at least one coding region or in a regulatory region operably linked to the at least one coding region, (ii) an exogenous polynucleotide that decreases the expression of the at least one coding region, or (iii) an edited genome that results in the decreased expression, wherein the edited genome comprises a mutation of the genomic DNA of the engineered cell compared to a control cell line.

15. The engineered cell line of claim 13 wherein the cells further comprise decreased expression of at least one additional coding region selected from Table I, increased expression of an miRNA selected from miR-520e, miR-1256, miR-520d-3p, miR-513a-5p, miR-519c-3p, miR-1270-2, miR-3187, miR-5763p, miR-22, miR-520c-3p, and miR-9 compared to a control cell line, decreased expression of an endogenous miRNA selected from Table IV, or a combination thereof.

16. The engineered cell line of claim 13 wherein the picornavirus is an enterovirus 71 or a poliovirus, chosen from either Sabin 1, Sabin 2, Sabin 3, Mahoney, Brunhilde, MEF-1, or Saukett.

17. A lysate of the engineered cell line of claim 13.

18. A method for producing a virus comprising:
providing the engineered cell line of claim 13;
incubating the engineered cell line under conditions suitable for the production of the picornavirus by the cells; and
harvesting the picornavirus produced by the cells.

19. The method of claim 18 wherein the incubating comprises a comprising (i) an RNA polynucleotide that inhibits expression of a coding region selected from Table I or (ii) a small molecule that inhibits expression of a coding region selected from Table I, or wherein the cells comprise an edited genome that results in decreased expression of a coding region selected from Table I.

20. The method of claim 18 wherein the picornavirus is an enterovirus 71 or a poliovirus, chosen from either Sabin 1, Sabin 2, Sabin 3, Mahoney, Brunhilde, MEF-1, or Saukett.

21. An engineered cell line, wherein cells of the engineered cell line comprise decreased endogenous expression of at least one coding region selected from Table I compared to a control cell line, wherein the cells comprise a mutation in the at least one coding region or in a regulatory region operably linked to the at least one coding region, and wherein the cells comprise a picornavirus.

22. The engineered cell line of claim 21 wherein the picornavirus is an enterovirus 71 or a poliovirus, chosen from either Sabin 1, Sabin 2, Sabin 3, Mahoney, Brunhilde, MEF-1, or Saukett.

23. The engineered cell line of claim 3 wherein the cells comprise a picornavirus.

24. The engineered cell line of claim 23 wherein the picornavirus is an enterovirus 71 or a poliovirus, chosen from either Sabin 1, Sabin 2, Sabin 3, Mahoney, Brunhilde, MEF-1, or Saukett.

25. A lysate of the engineered cell line of claim 2.

26. A lysate of the engineered cell line of claim 3.

\* \* \* \* \*

UNITED STATES PATENT AND TRADEMARK OFFICE
CERTIFICATE OF CORRECTION

PATENT NO. : 10,137,188 B2
APPLICATION NO. : 14/765365
DATED : November 27, 2018
INVENTOR(S) : Karpilow et al.

Page 1 of 1

It is certified that error appears in the above-identified patent and that said Letters Patent is hereby corrected as shown below:

In the Claims

Column 41, Line 64: Claim 1 'decreased endogenous expression' should read --decreased expression--

Column 42, Line 3: Claim 1 'decreased endogenous expression' should read --decreased expression--

Column 42, Line 8: Claim 2 'decreased endogenous expression' should read --decreased expression--

Column 42, Line 17: Claim 3 'decreased endogenous expression' should read --decreased expression--

Column 42, Line 31: Claim 4 'increased endogenous expression' should read --increased expression--

Column 42, Line 43: Claim 5 'decreased endogenous expression' should read --decreased expression--

Column 42, Line 49: Claim 5 'decreased endogenous expression' should read --decreased expression--

Column 43, Line 7: Claim 12 'increased endogenous expression' should read --increased expression--

Column 43, Line 14: Claim 13 'decreased endogenous expression' should read --decreased expression--

Column 44, Line 9: Claim 19 'comprises a comprising' should read --comprises--

Column 44, Line 19: Claim 21 'decreased endogenous expression' should read --decreased expression--

Signed and Sealed this
Seventh Day of May, 2019

Andrei Iancu
*Director of the United States Patent and Trademark Office*